(12) United States Patent
Kratz

(10) Patent No.: US 7,902,144 B2
(45) Date of Patent: Mar. 8, 2011

(54) THERAPEUTIC AND DIAGNOSTIC LIGAND SYSTEMS COMPRISING TRANSPORT MOLECULE BINDING PROPERTIES AND MEDICAMENTS CONTAINING THE SAME

(75) Inventor: Felix Kratz, Ihringen (DE)

(73) Assignee: KTB Tumorforschungsgesellschaft mbH, Freiburg Im Breisgau (DE)

( * ) Notice: Subject to any disclaimer, the term of this patent is extended or adjusted under 35 U.S.C. 154(b) by 0 days.

(21) Appl. No.: 10/221,544

(22) PCT Filed: Mar. 13, 2001

(86) PCT No.: PCT/EP01/02833

§ 371 (c)(1),
(2), (4) Date: Feb. 20, 2003

(87) PCT Pub. No.: WO01/68142

PCT Pub. Date: Sep. 20, 2001

(65) Prior Publication Data

US 2003/0185793 A1    Oct. 2, 2003

(30) Foreign Application Priority Data

Mar. 13, 2000    (DE) ................... 100 12 120

(51) Int. Cl.
*C07K 14/00* (2006.01)
*A61K 38/00* (2006.01)
*A61K 49/00* (2006.01)

(52) U.S. Cl. .................... 514/2; 530/300; 424/9.341
(58) Field of Classification Search ............. 514/2, 4, 514/6; 424/85.1; 530/350
See application file for complete search history.

(56) References Cited

U.S. PATENT DOCUMENTS

| 4,043,997 A * | 8/1977 | Schroeder ............. 530/364 |
| 5,157,044 A * | 10/1992 | Schoenwald et al. ...... 514/363 |
| 5,612,474 A | 3/1997 | Patel |
| 5,919,815 A | 7/1999 | Shashoua et al. |
| 6,267,964 B1 * | 7/2001 | Nygren et al. ........... 424/197.11 |
| 6,310,039 B1 * | 10/2001 | Kratz ................... 514/8 |

FOREIGN PATENT DOCUMENTS

| EP | 0 624 377 A | 11/1994 |
| WO | WO 91/05806 A | 5/1991 |
| WO | WO 96/39183 A | 12/1996 |
| WO | WO 98/08859 A | 3/1998 |
| WO | WO 00/02050 A | 1/2000 |

OTHER PUBLICATIONS

Trouet et al. Proc. Natl. Acad. Sci. vol. 79, pp. 626-629 (1982).*
Kratz et al. Biol. Pharm. Bull. 21(1): 56-61 (1998).*
Kratz, F. WO 98/10794.*
Penichet, M. et al. Journal of Immunology 163: 4421-4426 (1999).*
Minks, C. et al. Biochemistry 38: 10649-10659 (1999).*
Andresen, T. et al. Progress in Lipid Research 44: 68-97 (2005).*
Majumdar, S. et al. Advanced Drug Delivery Reviews 56: 1437-1452 (2004).*
Kratz, F. and Beyer, U. Drug Delivery 5: 281-299 (1998).*
Hudson, A. et al. International Journal of Pharmaceutics 182: 49-58 (1999).*
Abcam product datasheet for Transferrin Receptor antibody, ab25543 (Clone RVS10).*
Makrides et al., "Extended in vivo half-life of Human Soluble Complement Receptor Type 1 fused to a Serum Albumin-Binding Receptor", The Journal of Pharmacology and Experimental Therapeutics 277(1): 534-542 (1996).*
Nagy et al., "High yield conversion of doxorubicin to 2-pyrrolinodoxorubicin an analog 500-1000 times more potent: Structure-activity relationship of daunosamine-modified derivatives of doxorubicin", Proc. Natl. Acad. Sci. USA 93: 2464-2469 (1996).*

* cited by examiner

*Primary Examiner* — Anand U Desai
(74) *Attorney, Agent, or Firm* — Ropes & Gray LLP; Barbara A. Ruskin; Carl A. Morales

(57) ABSTRACT

The invention relates to transport molecule binding ligand compounds which comprise a therapeutically and/or diagnostically active substance and a carrier molecule-affine substance with a high association constant to the carrier molecule. The invention also relates to medicaments containing these ligand compounds and to diagnostic kits.

30 Claims, No Drawings

SEQUENCE LISTING

<160> NUMBER OF SEQ ID NOS: 82

<210> SEQ ID NO 1
<211> LENGTH: 8
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Gly at position 1 can be repeated for up to 20
      Gly residues.
<223> OTHER INFORMATION: Peptidase substrate.

<400> SEQUENCE: 1

Gly Pro Leu Gly Ile Ala Gly Gln
1               5

-continued

```
<210> SEQ ID NO 2
<211> LENGTH: 8
<212> TYPE: PRT
<213> ORGANISM: Artificial Sequence
<220> FEATURE:
<223> OTHER INFORMATION: Peptidase substrate.

<400> SEQUENCE: 2

Gly Pro Gln Gly Ile Trp Gly Gln
 1               5

<210> SEQ ID NO 3
<211> LENGTH: 8
<212> TYPE: PRT
<213> ORGANISM: Artificial Sequence
<220> FEATURE:
<223> OTHER INFORMATION: Peptidase substrate.

<400> SEQUENCE: 3

Gly Pro Leu Gly Met Trp Ser Arg
 1               5

<210> SEQ ID NO 4
<211> LENGTH: 6
<212> TYPE: PRT
<213> ORGANISM: Artificial Sequence
<220> FEATURE:
<223> OTHER INFORMATION: Peptidase substrate.

<400> SEQUENCE: 4

His Ser Ser Lys Leu Gln
 1               5

<210> SEQ ID NO 5
<211> LENGTH: 6
<212> TYPE: PRT
<213> ORGANISM: Artificial Sequence
<220> FEATURE:
<223> OTHER INFORMATION: Peptidase substrate.

<400> SEQUENCE: 5

Asn Ser Ser Tyr Phe Gln
 1               5

<210> SEQ ID NO 6
<211> LENGTH: 6
<212> TYPE: PRT
<213> ORGANISM: Artificial Sequence
<220> FEATURE:
<223> OTHER INFORMATION: Peptidase substrate.

<400> SEQUENCE: 6

Ser Ser Tyr Tyr Ser Gly
 1               5

<210> SEQ ID NO 7
<211> LENGTH: 4
<212> TYPE: PRT
<213> ORGANISM: Artificial Sequence
<220> FEATURE:
<223> OTHER INFORMATION: Peptidase substrate.

<400> SEQUENCE: 7

Gly Phe Leu Gly
 1

<210> SEQ ID NO 8
```

```
<211> LENGTH: 4
<212> TYPE: PRT
<213> ORGANISM: Artificial Sequence
<220> FEATURE:
<223> OTHER INFORMATION: Peptidase substrate.

<400> SEQUENCE: 8

Gly Phe Ala Leu
 1

<210> SEQ ID NO 9
<211> LENGTH: 4
<212> TYPE: PRT
<213> ORGANISM: Artificial Sequence
<220> FEATURE:
<223> OTHER INFORMATION: Peptidase substrate.

<400> SEQUENCE: 9

Ala Leu Ala Leu
 1

<210> SEQ ID NO 10
<211> LENGTH: 16
<212> TYPE: PRT
<213> ORGANISM: Artificial Sequence
<220> FEATURE:
<223> OTHER INFORMATION: Peptidase substrate.

<400> SEQUENCE: 10

Gly Pro Leu Gly Ile Ala Gly Gln Gly Pro Leu Gly Ile Ala Gly Gln
 1               5                  10                  15

<210> SEQ ID NO 11
<211> LENGTH: 12
<212> TYPE: PRT
<213> ORGANISM: Artificial Sequence
<220> FEATURE:
<223> OTHER INFORMATION: Peptidase substrate.

<400> SEQUENCE: 11

Phe Lys Phe Lys Phe Lys Phe Lys Phe Lys Phe Lys
 1               5                  10

<210> SEQ ID NO 12
<211> LENGTH: 5
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Gly at position 1 can be repeated for up to 20
      Gly residues.
<223> OTHER INFORMATION: Peptidase substrate.

<400> SEQUENCE: 12

Gly Phe Lys Phe Lys
 1               5

<210> SEQ ID NO 13
<211> LENGTH: 4
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: Polyoxyethylene glycol moiety added to
      N-terminal.
<223> OTHER INFORMATION: Peptidase substrate.

<400> SEQUENCE: 13
```

Phe Lys Phe Lys
1

<210> SEQ ID NO 14
<211> LENGTH: 4
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: N-acetyl derivative.
<223> OTHER INFORMATION: Carrier-molecule-affinitive substrate.

<400> SEQUENCE: 14

Ala Ala Ala Ala
1

<210> SEQ ID NO 15
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 15

Gly Leu Gly Leu
1

<210> SEQ ID NO 16
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 16

Ala Ala Ala Ala
1

<210> SEQ ID NO 17
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 17

Tyr Gly Gly Phe
1

<210> SEQ ID NO 18
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 18

Ala Gly Ser Glu
1

<210> SEQ ID NO 19
<211> LENGTH: 4
<212> TYPE: PRT
<213> ORGANISM: Artificial Sequence
<220> FEATURE:
<223> OTHER INFORMATION: Carrier-molecule-affinitive substrate.

```
<400> SEQUENCE: 19

Arg Gly Asp Ala
 1

<210> SEQ ID NO 20
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 20

Arg Gly Asp Cys
 1

<210> SEQ ID NO 21
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 21

Arg Gly Asp Ser
 1

<210> SEQ ID NO 22
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 22

Arg Gly Glu Ser
 1

<210> SEQ ID NO 23
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 23

Arg Gly Asp Val
 1

<210> SEQ ID NO 24
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 24

Gly Arg Gly Asp
 1

<210> SEQ ID NO 25
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 25
```

```
Lys Gly Asp Ser
 1

<210> SEQ ID NO 26
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 26

Gly Gly Tyr Arg
 1

<210> SEQ ID NO 27
<211> LENGTH: 4
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: N-acetyl derivative.
<223> OTHER INFORMATION: Carrier-molecule-affinitive substrate.

<400> SEQUENCE: 27

Ser Asp Lys Pro
 1

<210> SEQ ID NO 28
<211> LENGTH: 5
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: N-benzyloxycarbonyl derivative
<223> OTHER INFORMATION: Carrier-molecule-affinitive substrate.

<400> SEQUENCE: 28

Gly Gly Gly Gly Gly
 1               5

<210> SEQ ID NO 29
<211> LENGTH: 5
<212> TYPE: PRT
<213> ORGANISM: Artificial Sequence
<220> FEATURE:
<223> OTHER INFORMATION: Carrier-molecule-affinitive substrate.

<400> SEQUENCE: 29

Ala Gly Gly Gly Gly
 1               5

<210> SEQ ID NO 30
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 30

Ser Asp Gly Arg
 1

<210> SEQ ID NO 31
<211> LENGTH: 4
<212> TYPE: PRT
<213> ORGANISM: Artificial Sequence
<220> FEATURE:
```

```
<221> NAME/KEY: MOD_RES
<222> LOCATION: (1)...(1)
<223> OTHER INFORMATION: N-benzyloxycarbonyl derivative.
<223> OTHER INFORMATION: Carrier-molecule-affinitive substrate.

<400> SEQUENCE: 31

Gly Pro Leu Gly
 1

<210> SEQ ID NO 32
<211> LENGTH: 5
<212> TYPE: PRT
<213> ORGANISM: Artificial Sequence
<220> FEATURE:
<223> OTHER INFORMATION: Carrier-molecule-affinitive substrate.

<400> SEQUENCE: 32

Ala Ala Tyr Ala Ala
 1               5

<210> SEQ ID NO 33
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 33

Gly Gly Arg Ala
 1

<210> SEQ ID NO 34
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 34

Gly Gly Glu Ala
 1

<210> SEQ ID NO 35
<211> LENGTH: 5
<212> TYPE: PRT
<213> ORGANISM: Artificial Sequence
<220> FEATURE:
<223> OTHER INFORMATION: Carrier-molecule-affinitive substrate.

<400> SEQUENCE: 35

Gly Gly Gly Gly Gly
 1               5

<210> SEQ ID NO 36
<211> LENGTH: 6
<212> TYPE: PRT
<213> ORGANISM: Artificial Sequence
<220> FEATURE:
<223> OTHER INFORMATION: Carrier-molecule-affinitive substrate.

<400> SEQUENCE: 36

Gly Gly Gly Gly Gly Gly
 1               5

<210> SEQ ID NO 37
<211> LENGTH: 4
<212> TYPE: PRT
<213> ORGANISM: Artificial Sequence
```

```
<220> FEATURE:
<223> OTHER INFORMATION: Carrier-molecule-affinitive substrate.

<400> SEQUENCE: 37

Phe Gly Gly Phe
  1

<210> SEQ ID NO 38
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 38

Glu Ala Glu Asn
  1

<210> SEQ ID NO 39
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 39

Gly Arg Gly Asp
  1

<210> SEQ ID NO 40
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 40

Gly Pro Gly Gly
  1

<210> SEQ ID NO 41
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 41

Met Gly Met Met
  1

<210> SEQ ID NO 42
<211> LENGTH: 4
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: N-boc derivative.
<223> OTHER INFORMATION: Carrier-molecule-affinitive substrate.

<400> SEQUENCE: 42

Ala Gly Gly Gly
  1

<210> SEQ ID NO 43
<211> LENGTH: 4
<212> TYPE: PRT
```

```
<213> ORGANISM: Artificial Sequence
<220> FEATURE:
<223> OTHER INFORMATION: Carrier-molecule-affinitive substrate.

<400> SEQUENCE: 43

Phe Gly Phe Gly
 1

<210> SEQ ID NO 44
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 44

Pro Thr Pro Ser
 1

<210> SEQ ID NO 45
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 45

Val Gly Asp Glu
 1

<210> SEQ ID NO 46
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 46

Val Thr Lys Gly
 1

<210> SEQ ID NO 47
<211> LENGTH: 5
<212> TYPE: PRT
<213> ORGANISM: Artificial Sequence
<220> FEATURE:
<223> OTHER INFORMATION: Carrier-molecule-affinitive substrate.

<400> SEQUENCE: 47

Gly Gly Gly Gly Ala
 1               5

<210> SEQ ID NO 48
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 48

Asp Asp Asp Asp
 1

<210> SEQ ID NO 49
<211> LENGTH: 4
<212> TYPE: PRT
<213> ORGANISM: Artificial Sequence
<220> FEATURE:
```

```
<223> OTHER INFORMATION: Carrier-molecule-affinitive substrate.

<400> SEQUENCE: 49

Asp Ala Ser Val
 1

<210> SEQ ID NO 50
<211> LENGTH: 5
<212> TYPE: PRT
<213> ORGANISM: Artificial Sequence
<220> FEATURE:
<223> OTHER INFORMATION: Carrier-molecule-affinitive substrate.

<400> SEQUENCE: 50

Gly Gly Gly Gly Ala
 1               5

<210> SEQ ID NO 51
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 51

Val Thr Cys Gly
 1

<210> SEQ ID NO 52
<211> LENGTH: 4
<212> TYPE: PRT
<213> ORGANISM: Artificial Sequence
<220> FEATURE:
<221> NAME/KEY: MOD_RES
<222> LOCATION: (1)...(4)
<223> OTHER INFORMATION: All residues are D-isomers.
<223> OTHER INFORMATION: Carrier-molecule-affinitive substrate.

<400> SEQUENCE: 52

Val Val Val Val
 1

<210> SEQ ID NO 53
<211> LENGTH: 4
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: N-boc derivative.
<223> OTHER INFORMATION: Carrier-molecule-affinitive substrate.

<400> SEQUENCE: 53

Gly Gly Gly Lys
 1

<210> SEQ ID NO 54
<211> LENGTH: 4
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: N-boc derivative.
<223> OTHER INFORMATION: Carrier-molecule-affinitive substrate.

<400> SEQUENCE: 54

Phe Gly Gly Gly
 1
```

```
<210> SEQ ID NO 55
<211> LENGTH: 5
<212> TYPE: PRT
<213> ORGANISM: Artificial Sequence
<220> FEATURE:
<221> NAME/KEY: MOD_RES
<222> LOCATION: (5)...(5)
<223> OTHER INFORMATION: Residue at position 5 is D-isomer.
<223> OTHER INFORMATION: Carrier-molecule-affinitive substrate.

<400> SEQUENCE: 55

Ala Ala Ala Ala Glu
 1               5

<210> SEQ ID NO 56
<211> LENGTH: 5
<212> TYPE: PRT
<213> ORGANISM: Artificial Sequence
<220> FEATURE:
<223> OTHER INFORMATION: Carrier-molecule-affinitive substrate.

<400> SEQUENCE: 56

Ala Ala Ala Ala Glu
 1               5

<210> SEQ ID NO 57
<211> LENGTH: 5
<212> TYPE: PRT
<213> ORGANISM: Artificial Sequence
<220> FEATURE:
<223> OTHER INFORMATION: Carrier-molecule-affinitive substrate.

<400> SEQUENCE: 57

Ala Ala Ala Tyr Ala
 1               5

<210> SEQ ID NO 58
<211> LENGTH: 5
<212> TYPE: PRT
<213> ORGANISM: Artificial Sequence
<220> FEATURE:
<223> OTHER INFORMATION: Carrier-molecule-affinitive substrate.

<400> SEQUENCE: 58

Ala Ala Pro Ala Ala
 1               5

<210> SEQ ID NO 59
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 59

Ala Ala Tyr Ala
 1

<210> SEQ ID NO 60
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 60

Asp Ala His Lys
```

```
<210> SEQ ID NO 61
<211> LENGTH: 5
<212> TYPE: PRT
<213> ORGANISM: Artificial Sequence
<220> FEATURE:
<223> OTHER INFORMATION: Carrier-molecule-affinitive substrate.

<400> SEQUENCE: 61

Asp Ala Ser Gly Glu
 1               5

<210> SEQ ID NO 62
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 62

Glu Pro Glu Thr
 1

<210> SEQ ID NO 63
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 63

Glu Ser Leu Phe
 1

<210> SEQ ID NO 64
<211> LENGTH: 5
<212> TYPE: PRT
<213> ORGANISM: Artificial Sequence
<220> FEATURE:
<223> OTHER INFORMATION: Carrier-molecule-affinitive substrate.

<400> SEQUENCE: 64

Gly Gly Lys Ala Ala
 1               5

<210> SEQ ID NO 65
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 65

Gly Gly Tyr Ala
 1

<210> SEQ ID NO 66
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 66

Gly Leu Leu Gly
 1
```

```
<210> SEQ ID NO 67
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 67

Leu Leu Val Phe
 1

<210> SEQ ID NO 68
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 68

Lys Ala Phe Gly
 1

<210> SEQ ID NO 69
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 69

Lys Gly Gly Lys
 1

<210> SEQ ID NO 70
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 70

Phe Gln Gly Pro
 1

<210> SEQ ID NO 71
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 71

Pro Leu Gly Gly
 1

<210> SEQ ID NO 72
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 72

Thr Tyr Ser Lys
 1

<210> SEQ ID NO 73
```

```
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 73

Trp Gly Gly Tyr
 1

<210> SEQ ID NO 74
<211> LENGTH: 6
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: N-benzyloxycarbonyl derivative
<223> OTHER INFORMATION: Carrier-molecule-affinitive substrate.

<400> SEQUENCE: 74

Gly Gly Gly Gly Gly Gly
 1               5

<210> SEQ ID NO 75
<211> LENGTH: 4
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: N-benzyloxycarbonyl derivative.
<223> OTHER INFORMATION: Carrier-molecule-affinitive substrate.

<400> SEQUENCE: 75

Gly Pro Gly Gly
 1

<210> SEQ ID NO 76
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 76

Gly Gly Phe Met
 1

<210> SEQ ID NO 77
<211> LENGTH: 6
<212> TYPE: PRT
<213> ORGANISM: Artificial Sequence
<220> FEATURE:
<223> OTHER INFORMATION: Carrier-molecule-affinitive substrate.

<400> SEQUENCE: 77

Ala Ala Ala Pro Ala Ala
 1               5
```

```
<210> SEQ ID NO 78
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 78

Ala Leu Ala Gly
 1

<210> SEQ ID NO 79
<211> LENGTH: 5
<212> TYPE: PRT
<213> ORGANISM: Artificial Sequence
<220> FEATURE:
<221> NAME/KEY: MOD_RES
<222> LOCATION: (4)...(4)
<223> OTHER INFORMATION: Residue at position 4 is D-isomer
<223> OTHER INFORMATION: Carrier-molecule-affinitive substrate.

<400> SEQUENCE: 79

Gly Ala Ala Ala Ala
 1               5

<210> SEQ ID NO 80
<211> LENGTH: 6
<212> TYPE: PRT
<213> ORGANISM: Artificial Sequence
<220> FEATURE:
<223> OTHER INFORMATION: Carrier-molecule-affinitive substrate.

<400> SEQUENCE: 80

Ser Gly Ala Gly Ala Gly
 1               5

<210> SEQ ID NO 81
<211> LENGTH: 4
<212> TYPE: PRT
<213> ORGANISM: Artificial Sequence
<220> FEATURE:
<223> OTHER INFORMATION: Carrier-molecule-affinitive substrate.

<400> SEQUENCE: 81

Trp Gly Gly Tyr
 1

<210> SEQ ID NO 82
<211> LENGTH: 4
<212> TYPE: PRT
<213> ORGANISM: Artificial Sequence
<220> FEATURE:
<221> NAME/KEY: MOD_RES
<222> LOCATION: (1)...(1)
<223> OTHER INFORMATION: N-boc derivative.
<223> OTHER INFORMATION: Carrier-molecule-affinitive substrate.

<400> SEQUENCE: 82

Gly Gly Gly Gly
 1
```

THERAPEUTIC AND DIAGNOSTIC LIGAND SYSTEMS COMPRISING TRANSPORT MOLECULE BINDING PROPERTIES AND MEDICAMENTS CONTAINING THE SAME

DESCRIPTION

The present invention relates to carrier molecule-binding ligand compounds comprising a therapeutically and/or diagnostically active substance and a carrier-molecule-affinitive substance with a high association constant relative to the carrier molecule, as well as pharmaceutical products and diagnostic kits containing these ligand compounds.

A number of transport proteins for lipids, hormones, metabolites, pharmaceutical drugs, and vitamins circulate in the bloodstream. Examples of such transport proteins are albumin, haptoglobin, prealbumin, low-density lipoprotein (LDL), retinol-binding protein, transcortin, vitamin D-binding protein, or transcobalamin. The affinity between the transport protein and its ligand is described in particular by means of the association constant $K_A$.

It is known that a number of compounds, such as for example dyes, porphyrins, organic acids or pharmaceutical drugs, enter into a distinct noncovalent, i.e., physical interaction with certain transport proteins in the bloodstream, whereby a selectivity exists for certain transport proteins, for example for albumin.

For a number of blood proteins it is further known that they accumulate in pathogenic tissue, for example in malignant or inflamed tissue. For example, such accumulation has been demonstrated for the serum protein albumin (Kratz, F., Beyer U. (1998) Serum proteins as drug carriers of anticancer agents, a review. *Drug Delivery*, 5, 1-19).

The technical problem underlying the present invention is to therapeutically and diagnostically utilize the above-indicated carrier-molecule-binding properties, such as for example binding to transport proteins in the bloodstream due to distinct physical interactions, and to provide a new ligand system with carrier-molecule-binding properties and pharmaceutical products containing these carrier-molecule-binding compounds.

The solution to this technical problem is achieved by means of the embodiments of the present invention as characterized in the claims.

In particular, a carrier-molecule-binding ligand compound is provided that comprises at least one therapeutically or pharmaceutically and/or diagnostically active substance and at least one carrier-molecule-affinitive substance, having an association or binding constant $K_A$ relative to the carrier molecule of $>10^3$ M$^{-1}$, preferably $>10^5$ M$^{-1}$, even more preferably $>10^7$ M$^{-1}$, most preferably $>108$ M$^{-1}$, through a noncovalent bond.

The term "therapeutically or pharmaceutically active substance" means that the respective substance, either itself or after it is metabolized in the respective organism, has a pharmacological effect, and thus the term also comprises the derivatives resulting from these conversions. Of course, the therapeutically active substance can have a single pharmacological spectrum of action (for example, only as a cytostatic agent) or a broad pharmacological spectrum of action (for example, as a cytostatic agent and as an antirheumatic agent etc.). The term "diagnostically active substance" means that the respective substance is detectable, preferably also quantifiable, in the organism or parts thereof, such as for example cells and/or fluids, such as for example serum, by means of suitable chemical and/or physical measurement methods.

The carrier-molecule-affinitive substance in the carrier-molecule-binding ligand compound according to the invention has no covalent interaction with the carrier molecule, i.e., the carrier-molecule-affinitive substance binds to the carrier molecule on the basis of interactions of physical nature such as electrostatic interactions, hydrogen bonds, van der Waals bonds, and/or hydrophobic interactions. Moreover, with regard to the specificity of the carrier-molecule-affinitive substance (in respect) to the carrier molecule, it is crucial that the equilibrium constant of the association reaction between the carrier molecule and the carrier-molecule-affinitive substance be sufficiently high, which according to the invention corresponds to a value of $>10^3$ M$^{-1}$ (log $K_A>3$), preferably at least $10^4$ M$^{-1}$ (log $K_A$ at least 4), more preferably $>10^5$ M$^{-1}$ (log $K_A>5$), even more preferably $>10^7$ M$^{-1}$ (log $K_A>7$) at most preferably $>10^8$ M$^{-1}$ (log $K_A>8$). In the ligand compound according to the invention, the therapeutically and/or diagnostically active substance may be bound directly to the carrier-molecule-affinitive substance. In a preferred embodiment of the ligand compound according to the invention, the linkage between the therapeutically and/or diagnostically active substance and the carrier-molecule-affinitive substance either is not cleavable or this linkage is pH-dependent and/or enzymatically cleavable, within the body.

In a further preferred embodiment of the ligand compound according to the invention, the therapeutically and/or diagnostically active substance and the carrier-molecule-affinitive substance are bound to each other through a spacer molecule. Moreover, as already explained above for direct linkage between the therapeutically and/or diagnostically active substance and the carrier-molecule-affinitive substance, the spacer molecule and/or the linkage between the therapeutically and/or diagnostically active substance and the spacer molecule and/or the linkage of the carrier-molecule-affinitive substance and the spacer molecule either is uncleavable or the spacer molecule and/or the indicated linkages can be pH-dependent and/or enzymatically cleavable, within the body.

According to a further preferred embodiment, the direct linkage between the therapeutically and/or diagnostically active substance and the carrier-molecule-affinitive substance or the spacer molecule and/or the linkage between the therapeutically and/or diagnostically active substance and the spacer molecule and/or the linkage between the carrier-molecule-affinitive substance and the spacer molecule contains at least one acid-labile bond. Examples of such acid-labile bonds are ester, acetal, ketal, imine, hydrazone, carboxylhydrazone, or sulfonylhydrazone compounds.

According to a further embodiment of the ligand compound according to the invention, either the direct linkage between the therapeutically and/or diagnostically active substance and the carrier-molecule-affinitive substance or the spacer molecule and/or the linkage between the therapeutically and/or diagnostically active substance and the spacer molecule and/or the linkage between the carrier-molecule-affinitive substance and the spacer molecule contains at least one peptide bond. The peptide bond preferably is located within a peptide sequence which contains at least one protease cleavage sequence. Hence at least one peptide bond can be realized by addition of a peptide sequence into the direct linkage between the therapeutically and/or diagnostically active substance and the carrier-molecule-affinitive substance or into the spacer molecule and/or into the linkage between the therapeutically and/or diagnostically active substance and the spacer molecule and/or into the linkage between the carrier-molecule-affinitive substance and the spacer molecule, i.e., the respective linkage is a peptide bond, and preferably consists of about 1 to 30 amino acids. The peptide sequence is preferably tailored to the substrate specificity of certain endogenous enzymes or enzymes that occur in microorganisms or are formed therefrom. As a result, the peptide sequence or a portion of this sequence is recognized by enzymes within the body and the peptide is cleaved.

The enzymes are, for example, proteases and peptidases, for example matrix metalloproteases (MMP1-20), cysteine proteases (for example cathepsin B, D, L, H), aspartyl proteases (for example cathepsin D), serine proteases (for example plasmin, "tissue-type" plasminogen activator (tPA), "urokinase-type" plasminogen activator), kallikrein or kallikrein-like proteases (for example prostate-specific antigen), that in diseases such as rheumatoid arthritis or cancer are formed to an increased extent or are activated, which leads to excessive tissue decomposition, to inflammations, and to metastasizing. Target enzymes are in particular MMP-2, MMP-3 and MMP-9, cathepsins B, D, H and L, tissue-type plasminogen activator (tPA) and urokinase-type plasminogen activator as well as prostate-specific antigen, which have been identified as key enzymes in inflammatory and malignant diseases and participate in the indicated pathological processes as proteases (Vassalli, J., Pepper, M. S. (1994), *Nature* 370, 14-15; Brown, P. D. 1995), *Advan. Enzyme Regul.* 35, 291-301; Schmitt M., et al., J. *Obstetrics & Gynaecology*, 21, 151-65, 1995, T. T. Lah et al. (1998), *Biol. Chem.* 379, 125-301).

In a further embodiment of the ligand compound according to the invention, either the direct linkage between the therapeutically and/or diagnostically active substance and the carrier-molecule-affinitive substance or the spacer molecule and/or the linkage between the therapeutically and/or diagnostically active substance and the spacer molecule and/or the linkage between the carrier-molecule-affinitive substance and the spacer molecule contains at least one bond that is enzymatically cleavable but consists not of a peptide bond. Examples are carbamate bonds, for which the active substance or a derivative of the active substance is released by cleavage with disease-specific enzymes, for example, glutathione S transferases, glucuronidases, galactosidases.

All three types of bonds—acid-labile bond, peptide bond, enzymatically cleavable bond that does not contain a peptide bond-ensure that the therapeutically and/or diagnostically active substance or a corresponding active derivative is cleaved at the extracellular and/or intracellular site of action and the substance can exert its pharmaceutical and/or diagnostic effect.

The term "carrier molecule" comprises both natural and synthetic molecules that are suitable for transporting ligand compounds according to the invention, for example in body fluids such as blood serum. Suitable transport molecules are naturally occurring or synthetic macromolecules, for example polyethylene glycol (PEG) or dextran, and biological macromolecules such as proteins. Preferred proteins that are suitable as carrier molecules are selected from the group consisting of serum proteins. Albumin is an example of a preferred suitable serum protein. Further transport proteins suitable as carrier molecules are transferrin, haptoglobin, prealbumin, low-density lipoprotein (LDL), retinol-binding protein, transcortin, as well as vitamin D-binding protein or transcobalamin.

Suitable transport molecules are therefore naturally occurring or synthetic macromolecules, for example polysaccharides, polypeptides, polyalcohols, polyamines, dendrimers, copolymers, polyethylene glycol (PEG) or functionalized polyethylene glycols, and biological macromolecules such as proteins.

According to a preferred embodiment, the therapeutically and/or diagnostically active substance is a cytostatic agent, a cytokine, an immunosuppressant, an antirheumatic, an anti-inflammatory, an antibiotic; an analgesic, a virostatic or an antimycotic. Especially suitable cytostatics for the ligand compound of the present invention are the N-nitrosoureas such as nimustine, the anthracyclines doxorubicin, daunorubicin, epirubicin, idarubicin, mitoxantrone and ametantrone as well as related derivatives, the alkylating agents chlorambucil, bendamustine, melphalan and oxazophosphorines as well as related derivatives, the antimetabolites, for example purine antagonists or pyrimidine antagonists and folic acid antagonists such as methotrexate, 5-fluorouracil, 5'-deoxy-5-fluorouridine, gemcitabines and thioguanine as well as related derivatives, the taxanes paclitaxel and docetaxel as well as related derivatives, the camptothecines topotecan, irinotecan, 9-aminocamptothecine and camptothecine as well as related derivatives, the podophyllotoxin derivatives etoposide, teniposide and mitopodozide as well as related derivatives, the vinca alkaloids vinblastine, vincristine, vindesine, and vinorelbine as well as related derivatives, calicheamicins, maytansinoids, epithilones such as epithilone A and B and related derivatives, and platinum(II) complex compounds in the cis configuration, of general formulas I to XIV:

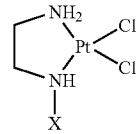

Formula I

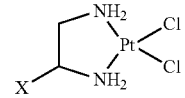

Formula II

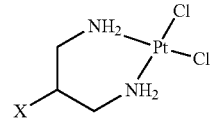

Formula III

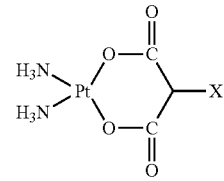

Formula IV

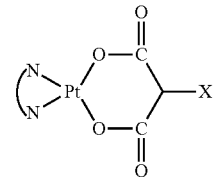

Formula V

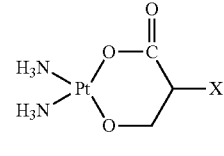

Formula VI

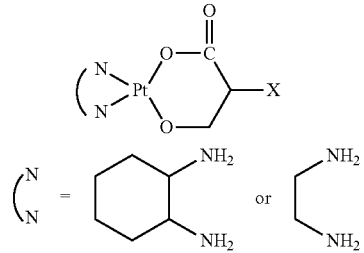

Formula VII

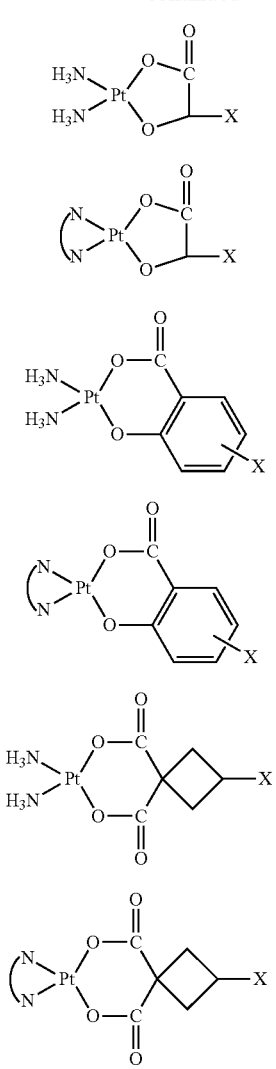

wherein X is the spacer molecule and/or the transport molecule-affinitive substance.

Particularly suitable cytokines in ligand compounds of the present invention are, for example, interleukin 2, interferon α-2a, interferon β-2b, interferon α-1a, interferon β-1b, interferon γ-1b and related derivatives. The cytokines used are, for example, genetically engineered pharmaceutical products.

Particularly suitable immunosuppressants in ligand compounds of the present invention are, for example, cyclosporin A, FK 506 (tacrolimus) and related derivatives.

Particularly suitable antirheumatics in conjugates of the present invention are, for example, methotrexate, sulfasalazine, chloroquine and related derivatives.

Particularly suitable antiinflammatories and/or analgesics in ligand compounds of the present invention are, for example, salicylic acid derivatives, such as acetylsalicylic acid and related derivatives, pharmaceutical drug derivatives having an acetic acid or propionic acid group such as diclofenac or indomethacin or ibuprofen or naproxen, and aminophenol derivatives such as paracetamol.

Particularly suitable antimycotics in ligand compounds of the present invention are, for example, amphotericin B and related derivatives.

Preferred virostatics in ligand compounds of the present invention are, for example, nucleoside analogs such as aciclovir, ganciclovir, idoxuridine, ribavirin, vidaribine, zidovudine, didanosine and 2',3'-dideoxycytidine (ddC) and related compounds, as well as amantadine.

Preferred antibiotics in the ligand compound according to the invention are sulfonamides, for example sulfanilamide, sulfacarbamide and sulfametoxydiazine and related derivatives, penicillins, for example 6-aminopenicillanic acid, penicillin G, as well as penicillin V and related derivatives, isoxazoyl penicillins such as oxacillin, cloxacillin and flucloxacillin as well as related derivatives, α-substituted benzylpenicillins such as ampicillin, carbenicillin, pivampicillin, amoxicillin and related derivatives, acylaminopenicillins, for example mezlocillin, azlocillin, piperacillin, apalcillin and related derivatives, amidino penicillins, for example mecillinam, a typical β-lactams such as imipenam and aztreonam, cephalosporins, for example cefalexin, cefradine, cefaclor, cefadroxil, cefixime, cefpodoxime, cefazolin, cefazedone, cefuroxime, cefamandol, cefotiam, cefoxitin, cefotetan, cefmetazole, latamoxef, cefotaxime, ceftriaxone, ceftizoxime, cefmenoxime, ceftazidime, cefsulodin and cefoperazone as well as related derivatives, tetracyclines such as tetracycline, chlortetracycline, oxytetracycline, demeclocycline, rolitetracycline, doxycycline, minocycline and related derivatives, chloramphenicols such as chloramphenicol and thiamphenicol as well as related derivatives, gyrase inhibitors, for example nalixidic acid, pipemidic acid, norfloxacin, ofloxacin, ciprofloxacin and enoxacin as well as related derivatives, and antituberculous agents such as isoniazid and related derivatives.

Of course, a single therapeutic and/or diagnostic species (for example, a therapeutic agent with a cytostatic as the therapeutically active substance) or different therapeutic and/or diagnostic species (for example, several different cytostatics or a cytostatic and an antirheumatic etc. as the therapeutically active substance) can be present bonded in the ligand compound according to the invention.

In a further preferred embodiment of the ligand compound according to the invention, the spacer molecule comprises a substituted or unsubstituted, branched-chain or unbranched-chain aliphatic alkyl residue and/or at least one substituted or unsubstituted aryl residue. The aliphatic alkyl residue preferably contains 1 to 20 carbon atoms, which can be partially replaced by oxygen or nitrogen atoms, for example to increase the water solubility, wherein such residues are preferably derived from an oligoethylene oxide or oligopropylene-oxide chain. Particularly suitable residues that are derived from oligoethylene oxide or oligopropylene oxide chains comprise, for example, diethylene glycol, triethylene glycol, tetraethylene glycol, pentaethylene glycol, hexaethylene glycol, heptaethylene glycol, and octaethylene glycol chains as well as analogous oligopropylene glycol chains. A preferred aryl residue is an unsubstituted or substituted phenyl residue, in which likewise one or more carbon atoms can be replaced by heteroatoms.

Preferred substituents of the aliphatic alkyl residue or the aryl residue are hydrophilic groups such as sulfonic acid (including salts thereof with alkali metals or alkaline earth metals), carboxyl (including salts thereof with alkali metals or alkaline earth metals), amino, aminoalkyl, and hydroxy groups.

Water solubility of the ligand compounds according to the invention can also be achieved or improved by the carrier-molecule-affinitive substance itself having one or more water-soluble groups, for example a sulfonic acid (including salts thereof with alkali metals or alkaline earth metals), carboxylic acid group (including salts thereof with alkali metals or alkaline earth metals), amino, aminoalkyl, and/or hydroxy groups, or by introducing such groups in synthesis steps.

Preferred diagnostically active substances of the ligand compound according to the invention contain, for example, one or more radionuclides, ligands comprising one or more radionuclides, preferably ligands complexing such radionuclides, one or more positron emitters, one or more NMR contrast media, one or more fluorescent compound(s), or one or more contrast media in the near IR region.

The ligand compound according to the invention, containing at least one therapeutically and/or diagnostically active substance (WS), at least one carrier-molecule-affinitive substance (TAS), and optionally a spacer molecule (SM), can be prepared according to one of the following general descriptions, depending on the functional group present.

Therapeutically and/or diagnostically active substances for the ligand compounds according to the invention that have one HOOC group can, for example, be derivatized as follows:

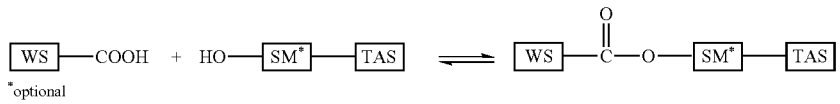

*optional

Esterification is carried out in this case by procedures well known in the prior art.

It is possible in addition to convert the HOOC group to a hydrazide group, for example by reaction with tert-alkylcarbazates followed by cleavage with acids (see DE-A-196 36 889), and to react the compound having a hydrazide group with a group containing a carbonyl component, consisting of the transport molecule-affinitive substance and the spacer molecule, as described inter alia in DE-A-196 36 889:

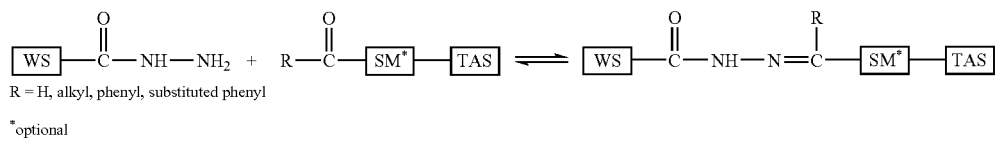

R = H, alkyl, phenyl, substituted phenyl

*optional

Therapeutically and/or diagnostically active substances for the ligand compounds according to the invention that have one H$_2$N group can, for example, be derivatized as follows:

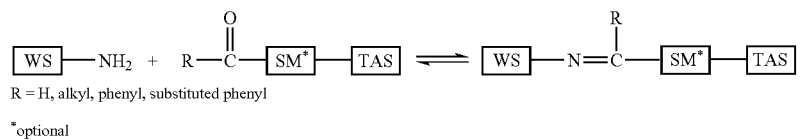

R = H, alkyl, phenyl, substituted phenyl

*optional

The reaction to form the imine derivatives is carried out in this case by procedures well known in the prior art.

Therapeutically and/or diagnostically active substances for the ligand compounds according to the-invention that have one HO— group can, for example, be derivatized as follows:

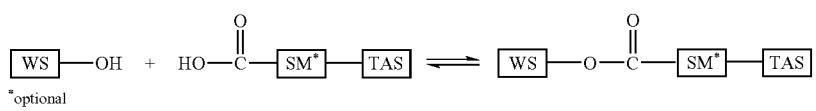

*optional

Esterification is carried out in this case by procedures well known in the prior art.

Therapeutically and/or diagnostically active substances for the ligand compounds according to the invention that have one carbonyl component can, for example, be derivatized as follows:

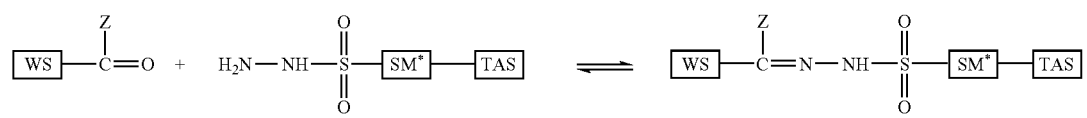

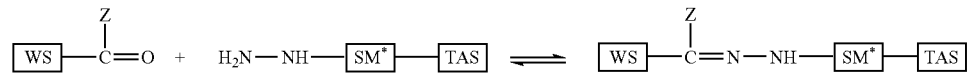

Z = chemical group of the therapeutically and/or diagnostically active substance
*optional The conversion to the carboxyhydrazone, sulfonylhydrazone, hydrazone, or imine derivatives is carried out in this case by procedures well known in the prior art.

Ligand compounds according to the invention that contain a peptide bond can, for example, be prepared by reacting a peptide, consisting of 2 to about 30 amino acids, with a carrier-molecule-affinitive compound, so that a carrier-molecule-affinitive compound is introduced directly or through a spacer molecule at the N-terminal end of the peptide.

The peptide derivatives obtained in this way, together with the therapeutic agent and/or diagnostic agent or derivatives thereof having an H$_2$N— or HO— group, can be converted to the corresponding ligand compounds according to the invention in the presence of a condensation agent such as for example N,N'-dicyclohexylcarbodiimide (DCC), N-cyclohexyl-N'-(2-morpholinoethyl)carbodiimide-metho-p-toluenesulfonate (CMC), (benzotriazol-1-yloxy)-trispyrrolidinophosphonium hexafluorophosphate (pyBOP) or O-benzotriazole-N,N,N',N'-tetramethyluronium hexafluorophosphate, and optionally with addition of a hydroxy compound such as for example N-hydroxysuccinimide, a water soluble N-hydroxysuccinimide such as for example N-hydroxysuccinimide-3-sulfonic acid sodium salt or 1-hydroxybenzotriazole, and/or in the presence of a base such as for example N-methylmorpholine or triethylamine:

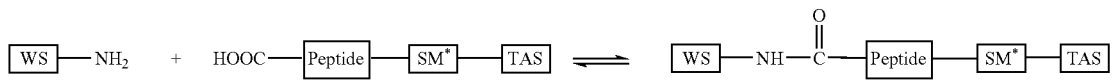

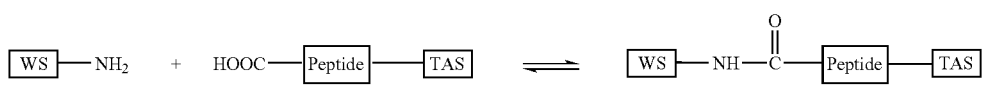

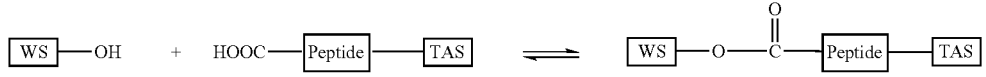

*optional

The substrate specificity of the target enzymes, such as for example MMP-2, MMP-3, MMP-9, cathepsin B, D, L and H, is well known (Netzel-Arnett et al. (1993), *Biochemistry* 32, 6427-6432, Shuja, S., Sheahan, K., Murname, M. J. (1991), *Int. J. Cancer* 49, 341-346, Lah, T. T., Kos, J. (1998), *Biol. Chem.* 379,125-130).

For example, octapeptides ($P_4$-$P'_4$) have been identified for MMP-2 and MMP-9 (see Table 1) which simulate the cleavage sequence of the collagen chain, and are particularly efficiently cleaved by MMP-2 and MMP-9:

TABLE 1

```
        Peptide
P4 P3 P2 P1 P'1 P'2 P'3 P'4
-------------------------------------------
Gly-Pro-Leu-Gly-Ile-Ala-Gly-Gln (SEQ ID NO: 1)

Gly-Pro-Gln-Gly-Ile-Trp-Gly-Gln (SEQ ID NO: 2)

Gly-Pro-Leu-Gly-Met-Trp-Ser-Arg (SEQ ID NO: 3)
```

(Netzel-Arnett et al., *Biochemistry* 32, 1993, 6427-6432)

The peptides are enzymatically cleaved exclusively at the $P_1$-$P'_1$-bond.

Substrate-specific hexapeptide sequences (P4-P2') are known for prostate-specific antigen (PSA), i.e., -His-Ser-Ser-Lys-Leu-Gln-(SEQ ID NO:4), Asn-Ser-Ser-Tyr-Phe-Gln- (SEQ ID NO:5) or -Ser-Ser-Tyr-Tyr-Ser-Gly- (SEQ ID NO:6) are known that are cleaved between P1 and P1' by PSA (Yang et al., J.Peptide Res. 54. 444-448, 1999; Denmeade et al., Cancer Res. 57, 4924-4930, 1997; Coombs et al., Chemistry & Biology 5, 475-488, 1998).

Furthermore, substrate-specific dipeptides are known for cathepsin with the sequence -Arg-Arg-, -Phe-Lys-, Gly-Phe-Leu-Gly, (SEQ ID NO:7) Gly-Phe-Ala-Leu (SEQ ID NO:8) or Ala-Leu-Ala-Leu (SEQ ID NO:9) (Werle, B., Ebert, E., Klein, W., Spiess, E. (1995), Biol. Chem. Hoppe-Seyler 376, 157-164; Ulricht, B., Spiess, E., Schwartz-Albiez, R., Ebert, W. (1995), Biol. Chem. Hoppe-Seyler 376, 404-414).

The peptide sequence containing the peptide cleavage site or predetermined breaking point relevant for the target enzyme can also be constructed so that the peptide cleavage site is multiply repeated, such as for example by:

```
                                    (SEQ ID NO: 10)
-Gly-Pro-Leu-Gly-Ile-Ala-Gly-Gln-Gly-Pro-
Leu-Gly-Ile-Ala-Gly-Gln or (SEQ ID NO: 11)
-Phe-Lys-Phe-Lys-Phe-Lys-Phe-
Lys-Phe-Lys-
``` or a repeating peptide sequence can be integrated that increases the distance between the thiol-binding groups and the relevant peptide cleavage sites, such as for example by: -(Gly)$_n$-Phe-Lys-Phe-Lys- (SEQ ID NO:12)

with preferably n=2 to 20, more preferably n≦12, or by an oxyethylene glycol unit as a water-soluble component
—(O—CH$_2$—CH$_2$)$_n$-Phe-Lys-Phe-Lys- (SEQ ID NO:13)
with preferably n=1 to 8.

An important feature of this embodiment of the ligand compound according to the invention is the fact that the peptide cleavage site relevant for the respective target enzyme occurs at least once in an oligopeptide consisting of about 1 to 30 amino acids.

The oligopeptides indicated above are representative examples for the enzymatically cleavable bond in the ligand compounds according to the invention. The proteases indicated above are examples of disease-associated enzymes. The therapeutic preparation can be independently used for other disease-associated proteases.

Therapeutic or diagnostic derivatives of the ligand compounds according to the invention that contain a cytokine can, for example, be prepared by reacting the cytokine with a spacer molecule-linked carrier-molecule-affinitive substance which has a carboxylic acid or an activated carboxylic acid group:

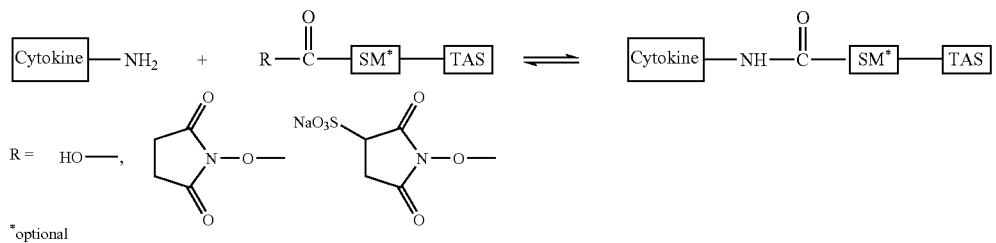

If the spacer molecule has an N-hydroxysuccinimide ester group (N-hydroxysuccinimide or the sodium salt of N-hydroxysuccinimide-3-sulfonic acid), then it is directly reacted with the cytokine. The reaction of cytokine with a spacer-linked carrier-molecule-affinitive substance having a carboxylic acid group, to form the corresponding carrier-molecule-affinitive cytokine derivatives, is carried out in the presence of a condensation agent such as for example N,N'-dicyclohexylcarbodiimide (DCC) or N-cyclohexyl-N'-(2-morpholinoethyl)-carbodiimide-metho-p-toluenesulfonate (CMC), and optionally with addition of N-hydroxysuccinimide or the sodium salt of N-hydroxysuccinimide-3-sulfonic acid. Cytokines derivatized in this way are purified, -for example, using size-exclusion chromatography. The conversions described above are well known in the prior art (for example, see Bioconjugate Techniques, G. T. Hermanson, Academic Press, 1996).

Preferred carrier-molecule-affinitive substances in the ligand compound according to the invention are selected from the group consisting of phthalocyanines, coumarins, flavonoids, tetracyclines, naphthalenes, aryl- and heteroarylcarboxylic acids, lipids and fatty acids, for example long-chain fatty acids such as $C_{16}$-$C_{20}$ fatty acids, cyclic or linear tetrapyrroles and organometallic compounds thereof, for example porphyrins and protoporphyrins (for example, bilirubin and derivatives thereof, hematin and derivatives thereof, aromatic acid derivatives substituted with 2-5 halogen atoms (Cl, Br or I) such as iophenoxic acid, organic dyes, for example Evans blue and bromcresol dyes such as bromcresol green and bromcresol purple, and the tryptophan and thyroxine analog compounds as well as derivatives of the above-indicated classes of compounds. Furthermore, the organic dyes used as carrier-molecule-affinitive substances can be chemically modified or derivatized before or after binding to the therapeutically and/or diagnostically active substance or to the spacer molecule, whereby however the binding behavior is maintained as compared with the unmodified compound with the carrier molecule. As an example, a dye used as a carrier-molecule-affinitive substance, for example an azo dye, may be derivatized by the above-indicated chemical modification, for example by reduction of the azo group or by replacement of the azo group by a C—C single bond or a C—C double bond, in such a way that it is no longer colored.

Examples of carrier-molecule-affinitive substances in the ligand compound according to the invention are selected from the following groups:

naphthalene and naphthyl derivatives: for example
1,4,5,8-NAPHTHALENETETRACARBOXYLIC ACID, NAPHTHOL,
1,1'-(1,5-NAPHTHALENEDIYL)BIS(3-CYCLOHEXYLUREA),
4-ACETAMIDO-5-HYDROXY-2,7-NAPHTHALENE DISULFONIC ACID,
2-(2-HYDROXY-1-NAPHTHYLMETHYLENEAMINO) BENZOIC ACID,
9-FLUORENYLIDENEAMINO N-(1-NAPHTHYL)CARBAMATE,
2-(N-(1-NAPHTHYL)CARBAMOYL)CYCLOHEXANECARBOXYLIC ACID,
1,1'-(1,5-NAPHTHALENEDIYL)BIS(3-(3-PYRIDYLMETHYL)UREA),
1,1'-(1,5-NAPHTHALENEDIYL)BIS(3-BENZYLUREA),
2,2'-OXYBIS(ACETIC ACID (2-HYDROXY-1-NAPHTHYLMETHYLENE)HYDRAZIDE),
ADIPIC ACID BIS((1-NAPHTHYLMETHYLENE)HYDRAZIDE),
3-(N-PHENYLCARBAMOYL)-2-NAPHTHYL N-(5-CHLORO-2-METHOXYPHENYL)CARBAMATE,
6-BENZOYL-2-NAPHTHYL PHOSPHATE, SODIUM SALT,
L-ARGININE 4-METHOXY-BETA-NAPHTHYLAMIDE HYDROCHLORIDE,
1-AMINO-8-NAPHTHOL-2,4-DISULFONIC ACID,
FMOC-D-2-NAPHTHYLALANINE, LYS-ALA 4-METHOXY-BETA-NAPHTHYLAMIDE DIHYDROCHLORIDE,
4-(1,8-DIHYDROXY-3,6-DISULFO-2-NAPHTHYLAZO)-SALICYLIC ACID,
1,1'-HEXAMETHYLENEBIS(3-(1-NAPHTHYLMETHYL)UREA),
CARBOBENZYLOXYTRYPTOPHAN BETA-NAPHTHYLAMIDE,
3-(N-(2-METHOXYPHENYL)CARBAMOYL)-2-NAPHTHYL N-(5-CHLORO-2-METHOXYPHENYL)CARBAMATE,
2-(1-NAPHTHYL)-2-PHENYLACETIC ACID, 8-[(2-CARBOXYETHYL)THIO]-1-NAPHTHOIC ACID,
3-[1-(2-CARBOXYETHYL)-2-OXO-1,2-DIHYDROACENAPHTHYLEN-1-YL]PROPANOIC ACID, 3-[(1-NAPHTHYLAMINO)CARBONYL]BICYCLO[2.2.1]-HEPT-5-ENE-2-CARBOXYLIC ACID,
N'',N'''-DI[1-(2-NAPHTHYL)ETHYLIDENE]CARBONIC ACID DIHYDRAZIDE,
4-[[4-(2-NAPHTHYL)-1,3-THIAZOL-2-YL]AMINO]-4-OXOBUTANOIC ACID,
FMOC-L-2-NAPHTHYLALANINE, 1,4,5,8-NAPHTHALENETETRACARBOXYLIC ACID HYDRATE,
BIS(2-NAPHTHYL) N,N'-(4-METHYL-1,3-PHENYLENE)BISCARBAMATE,
8-HYDROXY-5-(1-NAPHTHYLAZO)-2-NAPHTHALENESULFONIC ACID, SODIUM SALT,
N'1,N'3-DI(1-NAPHTHYLMETHYLIDENE)-2-BUTYL-PROPANEDIOIC HYDRAZIDE,
(+/−)-1,1'-BINAPHTHYL-2,2'-DICARBOXYLIC ACID,
(+/−)-2,2'-DIMETHOXY-1,1'-BINAPHTHYL-3,3'-DICARBOXAMIDE,
1-HYDROXY-4-(1-PHENYL-1H-TETRAZOL-5-YL-THIO)-2-NAPHTHOIC ACID, 3,3'-DIPHENYL-(1,1)BINAPHTHALENYL-2,2'-DICARBOXYLIC ACID,
2,6-DIMETHOXY-4-OXO-3,5-DIOXA-PHOSPHA-CYCLOHEPTA(2,1-A,3,4-A')DINAPHTHALEN-4-OL,
4-((BR-4-ME-PHENYLIMINO)-ME)-3-HO-NAPHTHALENE-2-CARBOXYLIC ACID (2-MEO-PH)AMIDE,
8-([2-[(METHYLAMINO)CARBONYL]PHENYL]THIO)-1-NAPHTHOIC ACID,
N-GLUTARYL-L-PHENYLALANINE-BETA-NAPHTHYLAMIDE,
2-HYDROXY-3-NAPHTHOIC ACID 2-AMINOANTHRAQUIINONYLAMIDE PHOSPHATE,
2-HYDROXY-3-NAPHTHOIC ACID 2-AMINOAZOBENZANILIDE PHOSPHATE,
3-(5-(2-CARBOXYETHANESULFONYL)NAPHTHALENE-1-SULFONYL) PROPIONIC ACID,
4-((4-CL-PHENYLIMINO)-ME)-3-HO-NAPHTHALENE-2-CARBOXYLIC ACID (2-MEO-PH)-AMIDE,
4-HYDROXY-7-METHOXY-1-(3-METHOXY-PHENYL)-NAPHTHALENE-2-CARBOXYLIC ACID,
3,6-DISULFO-NAPHTHALENE-1,8-DICARBOXYLIC ACID, L-ALA-ALA-L-PHE-ALPHA-NAPHTHYLAMIDE,
CBZ-L-TH R-L-VAL-BETA-NAPHTHYLAMIDE, CBZ-GLY-L-VAL-BETA-NAPHTHYLAMIDE,
CBZ-ILE-L-ALA-BETA-NAPHTHYLAM IDE, CBZ-L-ALA-THR-BETA-NAPHTHYLAMIDE,
DISODIUM 4-(BENZOYLAMINO)-5-METHYL-2,7-NAPHTHALENEDISULFONATE,
NAPHTHALENE-1,4,8-TRICARBOXYLIC ACID,
2-[[2-(1-NAPHTHYL)ACETYL]AMINO]SUCCINIC ACID,
(10-HO-10-PH-4H-8-THIA-7, 10A-DIAZA-PENTALENO (1,2-A)NAPHTHALEN-9-YL)ACETIC ACID,
1-(NAPHTHALENE-2-CARBONYL)-3-NAPHTHALEN-2-YLUREA,
1-(3-METHOXY-PHENYL)-3-(NAPHTHALENE-1-CARBONYL)THIOUREA, (S)—N—(1-(1-NAPHTHYL)ETHYL)SUCCINAMIC ACID,
L-LYSYL-L-ALANINE-4-METHOXY-BETA-NAPHTHYLAMIDE HYDROBROMIDE,
5-((2-(T-BOC)-GAMMA-GLUTAMYLAMINOETHYL)AMINO)NAPHTHALENE-1-SULFONIC ACID,
8-([2-[(ACETYLOXY)METHYL]PHENYL]THIO)-1-NAPHTHOIC ACID,
2-[[(9H-FLUOREN-9-YLMETHOXY)CARBONYL]AMINO]-3-(2-NAPHTHYL)PROPANOIC ACID,
I-NAPHTHYLACETYLSPERMINE TRIHYDROCHLORIDE,
4-[(2-ETHOXY-2-OXOETHYL)THIO]NAPHTHALENE-1,8-DICARBOXYLIC ACID, FMOC-(R)-3-AMINO-4-(2-NAPHTHYL)BUTYRIC ACID, 2,2'-BIQUINONYL DICARBOXYLIC ACID;
benzophenone derivatives: for example
BENZOPHENONE 2,4'-DICARBOXYLIC ACID,
3,3',4,4'-BENZOPHENONE TETRACARBOXYLIC ACID,
2',3,4-BENZOPHENONE TRICARBOXYLIC ACID,
2,2'-DIHYDROXY-4,4'-DIMETHOXY-5-SULFOBENZOPHENONE,
4-[N-[2-(ACETAMIDO)ETHYL]-N-METHYLAMINO]-2'-CARBOXY-2-HYDROXYBENZOPHENONE;
phthalimide and isophthalimide derivatives and phthalic acid and isophthalic acid derivatives: for example
5-SULFOISOPHTHALIC ACID MONOSODIUM SALT, 2-PHENYL-3-PHTHALIMIDOQUINOLINE-4-CARBOXYLIC ACID,
2-PHTHALIMIDOGLUTARIC ACID,
2,5-BIS(2-HYDROXYETHYLAMINO)TEREPHTHALIC ACID,
2- and/or 4-SULFOTEREPHTHALIC ACID,
5-SULFOISOPHTHALIC ACID,
2,5-BIS(N-(2,5-XYLYL)CARBAMOYL)TEREPHTHALIC ACID,
4-[(2-CARBOXYPHENYL)THIO]ISOPHTHALIC ACID,
4-(4-ACETYL-3-HYDROXY-2-PROPYLPHENOXY) ISOPHTHALIC ACID, 2,4,6-TRIMETHYLANILINE SALT,
4-(N-(4-METHOXYPHENYL)CARBAMOYL)ISOPHTHALIC ACID,
PHTHALIC ACID MONO-((2-CHLOROPHENYL)PHENYLMETHYL) ESTER,
4-(4-(3,4-DIMETHYLPHENYLSULFANYL)BENZENESULFONYL)PHTHALIC ACID,
4-(4-(4-CARBOXYPHENOXY)-BENZOYL)PHTHALIC ACID,
4-(4-CHLORO-BENZOYL)PHTHALIC ACID,
5-(5-(4-HYDROXYPHENYL)-3-PHENYL-4,5-DIHYDROPYRAZOL-1-YL)ISOPHTHALIC ACID,
5-(5-(4-DIMETHYLAMINO-PH)-3-PHENYL-4,5-DIHYDRO-PYRAZOL-1-YL)ISOPHTHALIC ACID,
PHTHALIC ACID MONO-(BIPHENYL-4-YL-PHENYLMETHYL) ESTER, PHTHALIC ACID. MONO-(1-METHYL-2,2-DIPHENYLETHYL) ESTER,
4,5-BIS-(4-AMINOPHENOXY)PHTHALIC ACID,
4,5-DI(4-METHOXYPHENOXY)PHTHALIC ACID;
quinoline and isoquinoline derivatives: for example
N,N'-BIS(8-QUINOLYLOXYCARBONYL)-4-METHYL-1,3-PHENYLENEDIAMINE, 3,3'-BIS(2-(2-QUINOLYL)VINYL)AZOBENZENE,
8-SULFO-2,4-QUINOLINEDICARBOXYLIC ACID,
2-[4-(ACETYLAMINO)PHENYL]-7-METHYLQUINOLINE-4-CARBOXYLIC ACID,
3-(1,3-DIOXO-1H,3H-BENZO(DE)ISOQUINOLIN-2-YL) BENZOIC ACID, DISODIUM 3-METHYL-4-(QUINOLIN-2-YLMETHYLENE)PENT-2-ENEDIOATE,
2-(5-CARBOXY-PENTYL)-3-PH-1-PR-5,6,7,8-TETRAHYDRO-ISOQUINOLINIUM,
1-(1H-INDOL-3-YL)-1H-ISOQUINOLINE-2-CARBOXYLIC ACID PHENYLAMIDE,
1-ET-6-F-4-OXO-7-(4-(2-OXO-PR)-PIPERAZIN-1-YL)-2H-QUINOLINE-3-CARBOXYLIC ACID,
N-ETHYL-3-(PYRIDIN-2-YL)-4-(QUINOLIN-4-YL) PYRAZOLE-1-CARBOXAMIDE,
2-[4-[(5-CHLORO-2-QUINOLYL)OXY]PHENOXY]PROPANOIC ACID,
N2-[2-[(3-CYANO-4-METHYL-2-QUINOLYL)THIO] PHENYL]-2-FURAMIDE,
3-(1-[1,1'-BIPHENYL]-4-YL-1H-1 ,2,3,4-TETRAAZOL-5-YL)QUINOLIN-4(1H)-ONE, FMOC-BETA-(2-QUINOLYL)-ALA-OH,
N-BENZYL-2-[(4-METHYL-5-QUINOLIN-6-YL-4H-1,2,4-TRIAZOL-3-YL)THIO]ACETAMIDE,
FMOC-ALA(3'-QUINOYL)-OH,
FMOC-(S)-2-TETRAHYDROISOQCUINOLINE ACETAMIDE;
anthraquinone derivatives: for example
1,8-BIS(BENZAMIDO)ANTHRAQUINONE,
N,N'-1,5-ANTHRAQUINONYLENE DIANTHRANILIC ACID;
anthracene derivatives: for example
2-(7-OXO-7H-BENZ(DE)ANTHRACEN-3-YLTHIO) ACETIC ACID,
9,10-DIHYDRO-9,10-DIOXO-2,3-ANTHRACENEDICARBOXYLIC ACID,
9-HYDROXYIMINO-9,10-DIHYDRO-ANTHRACENE-1-CARBOXYLIC ACID;
phenanthrene and phenanthroline derivatives: for example
1,10-PHENANTHROLINE-2,9-DICARBOXYLIC ACID,
4-P-TOLYL-1,10-PHENANTHROLINE-2,9-DICARBOXYLIC ACID,
1,2,3,4-TETRAHYDRO-PHENANTHRENE-1,2-DICARBOXYLIC ACID,
benzylidene derivatives: for example
2,2'-OXYDIACETIC ACID BIS((4-ACETAMIDOBENZYLIDENE) HYDRAZIDE),
2-(FURFURYLUREIDO)ACETIC ACID N2-(4-HYDROXY-3-METHOXYBENZYLIDENE) HYDRAZIDE,
2-(3-(3,4-DICHLOROPHENYL)UREIDO)ACETIC ACID (5-BROMO-2-HYDROXYBENZYLIDENE) HYDRAZIDE,
2-(3-(2-ETHOXYPHENYL)UREIDO)ACETIC ACID (3,4-DIMETHOXYBENZYLIDENE) HYDRAZIDE,
2-(3-(4-METHOXYPHENYL)UREIDO)ACETIC ACID (2,3,4-TRIMETHOXYBENZYLIDENE)HYDRAZIDE,
4-(3-(2-FLUOROPHENYL)UREIDO)BENZOIC ACID (3,4-DICHLOROBENZYLIDENE)HYDRAZIDE,
4-(3-(2-FLUOROPHENYL)UREIDO)BENZOIC ACID (4-METHYLBENZYLIDENE)HYDRAZIDE,
4-(3-(2-FLUOROPHENYL)UREIDO)BENZOIC ACID (4-METHOXYBENZYLIDENE)HYDRAZIDE,
4-(3-(2-FLUOROPHENYL)UREIDO)BENZOIC ACID (4-HYDROXY-3-METHOXYBENZYLIDENE)HYDRAZIDE,
4-(3-(2-FLUOROPHENYL)UREIDO)BENZOIC ACID (4-ACETAMIDOBENZYLIDENE)HYDRAZIDE,
4-(3-(2-FLUOROPHENYL)UREIDO)BENZOIC ACID (3,4-DIMETHOXYBENZYLIDENE)HYDRAZIDE,
2-(2-CHLOROBENZAMIDO)BENZOIC ACID (2-CHLORO-4-(DIMETHYLAMINO)BENZYLIDENE) HYDRAZIDE,
2-(3-(3-CHLOROPHENYL)UREIDO)ACETIC ACID (4-BUTOXYBENZYLIDENE)HYDRAZIDE,
2-(3-(6-METHYL-2-PYRIDYL)UREIDO)ACETIC ACID (3,4-DIMETHOXYBENZYLIDENE)HYDRAZIDE,
2-(3-(2-ETHOXYPHENYL)UREIDO)ACETIC ACID (2-HYDROXYBENZYLIDENE)HYDRAZIDE,
2-(3-(2-ETHOXYPHENYL)UREIDO)ACETIC ACID (4-ACETAMIDOBENZ-YLIDENE)HYDRAZIDE,
N'1-(4-CHLOROBENZYLIDENE)-3-[5-(2,3-DICHLOROPHENYL)-2H-1,2,3,4-TETRAAZOL-2-YL],
N'1-BENZYLIDENE-2-[3-[(4-METHYL-1,3-THIAZOL-2-YL)METHYL]-4-OXO-3,4-DIHYDROPHTHAL,
2,6-BIS(4-ACETAMIDOBENZYLIDENE)-1-CYCLOHEXANONE,
N-BENZOYLANTHRANILIC ACID (4-HYDROXY-3-METHOXYBENZYLIDENE)HYDRAZIDE,
4-(3-(3-CHLOROPHENYL)UREIDO)BENZOIC ACID (3-ETHOXY-4-HYDROXY-BENZYLIDENE)HYDRAZIDE,
4-(3-(3-CHLOROPHENYL)UREIDO)BENZOIC ACID (4-ETHOXY-3-METHOXYBENZYLIDENE)HYDRAZIDE,
4-(3-(3-CHLOROPHENYL)UREIDO)BENZOIC ACID (2-CHLORO-4-(DIMETHYLAMINO)BENZYLIDENE) HYDRAZIDE,
4-(3-(3-CHLOROPHENYL)UREIDO)BENZOIC ACID (3,4-DICHLOROBENZYLIDENE)HYDRAZIDE,
4-FLUOROBENZYL N-(4-METHOXYBENZYLIDENE)-[(ANILINOCARBONYL)AMINO]METHANEHYDRAZONO,
2-((2-HO-BENZYLIDENE)-AMINO)-5-(N'-(2-HO-BENZYLIDENE)-GUANIDINO)PENTANOIC ACID,
2,3-BIS-(3-METHOXYBENZYLIDENE)SUCCINIC ACID, 2,3-BIS-(3,4-DIMETHOXYBENZYLIDENE)SUCCINIC ACID,
2,3-BIS-(4-CHLOROBENZYLIDENE)SUCCINIC ACID,
2,3-DIBENZYLIDENE SUCCINIC ACID,
BENZYLIDENE CBZ-NEURAMINIC ACID,
3-HYDROXY-2-((2-HYDROXYBENZYLIDENE) AMINO)-3-PHENYLPROPIONIC ACID,
3-HO-3-(4-((2-HO-BENZYLIDENE)-AMINO)-PH)-2-PHENYLACETYLAMINOPROPIONIC ACID;
diphenyl and biphenyl derivatives: for example
3-CHLORO-4-BIPHENYLYLN-(2,5-DIMETHOXYPHE-NYL)CARBAMATE,
2'-BENZOYL-2-BIPHENYLCARBOXYLIC ACID,
2'-[(4-FLUOROANILINO)CARBONYL][1,1'-BIPHENYL]-2-CARBOXYLIC ACID,
3-(2,4,6-TRIMETHYLBENZOYL)-2-BIPHENYLCAR-BOXYLIC ACID,
2'-BENZYLCARBAMOYLBIPHENYL-2-CARBOXYLIC ACID,
3-CHLORO-3'-METHYLBIPHENYL-2,2'-DICARBOXY-LIC ACID,
2-HO-5-(4'-HO-BIPHENYL-4-YLAZO)BENZOIC ACID,
2-[([1,1'-BIPHENYL]-4-YLAMINO)CARBONYL]BEN-ZOIC ACID,
3-(1-[1,1'-BIPHENYL]-4-YL-1H-1,2,3,4-TETRAAZOL-5-YL)QUINOLIN-4(1H)-ONE, 2-[[(3-[1,1'-BIPHENYL]-4-YL-3-OXOPROPYLIDENE)AMINO]OXY]-N-(5-IODO-2-PYRIDINYL)ACETIC ACID,
4,4'-DI-BOC-DIAMINOBIPHENYL-2,2'-DICARBOXY-LIC ACID,
2,3,2'-BIPHENYLTRICARBOXYLIC ACID,
3-CHLORO-4-BIPHENYLYLN-(2,5-DIMETHOXYPHE-NYL)CARBAMATE,
4,4'-BIS(3-(3-PYRIDYL)UREIDO)DIPHENYL-METHANE,
4,4'-BIS(3-METHYL-3-PHENYLUREIDO)DIPHENYL-METHANE,
4,4'-METHYLENEBIS(1,3-DIPHENYL-1-ETHY-LUREA),
2,2'-CARBOXYDIPHENYLSULFONE, 2,3-DIPHENYL-SUCCINIC ACID,
1,3-DIPHENYL-1-(2-MORPHOLINO-1-CYCLO-PENTEN-1-YLCARBONYL)UREA,
2-BENZOYLAMINO-3-(DIPHENYLPHOSPHINOYL)-3-PHENYL-ACRYLIC ACID, MESO-2,3-DIPHENYL-SUCCINIC ACID,
4,5-DIPHENYL-2,3-DIHYDRO-1H-PYRAZOLO[3,4-C]PYRIDAZIN-3-ONE,
2-HYDROXY-2,2-DIPHENYLACETIC ACID (1-(4-BRO-MOPHENYL)ETHYLIDENE)HYDRAZIDE,
2,5-DIPHENYLFURAN-3,4-DICARBOXYLIC ACID,
1-(2,3-DIPHENYLACRYLOYL)-3-(4-METHOXYPHE-NYL)-THIOUREA, N1-[2-(1,3-DIPHENYL-1H-4-PYRAZOLYL)-1-(HYDRAZINOCARBONYL)VI-NYL]-2,4-DICHLOROBENZOIC ACID,
N1-[1-[(BENZYLAMINO)CARBONYL]-2-(1,3-DIPHE-NYL-1H-PYRAZOL-4-YL)VINYL]BENZAMIDE,
N2-ACETYL-O6-(DIPHENYLCARBAMOYL)GUA-NINE;
tryptophan and indole derivatives: for example
5-BENZYLOXYINDOLE-3-ACETIC ACID,
6-BENZAMIDO-N-(2-(3-INDOLYL)ETHYL)HEXANA-MIDE, N-(3-INDOLYLACETYL)-DL-ASPARTIC ACID,
INDOLE-3-ACETYL-L-ASPARTIC ACID,
4-(3-INDOLYLMETHYLAMINO)BENZOIC ACID,
2-(2,2-BIS(1H-INDOL-3-YL)-ETHYL)PHENYLAMINE,
2-((5-BROMO-1,3-DIOXO-1,3-DIHYDRO-ISOINDOL-2-YLMETHYL)AMINO)BENZOIC ACID,
3-(2-(2-CARBOXYBENZOYLAMINO)ETHYL)-5-CHLORO-1H-INDOLE-2-CARBOXYLIC ACID,
3-PHENYL-PYRROLO(2,1,5-CD)INDOLIZINE-1,2-DI-CARBOXYLIC ACID,
(R,S)-FMOC-1,3-DIHYDRO-2H-ISOINDOLE CAR-BOXYLIC ACID,
1-(1H-INDOL-3-YL)-1H-ISOQUINOLINE-2-CARBOXY-LIC ACID PHENYLAMIDE,
N'-2-[[4-(DIMETHYLAMINO)PHENYL]METHYLENE]-3-PHENYL-1H-INDOLE-2-CARBOHYDRAZIDE,
INDOLE-3-ACETYL-DL-TRYPTOPHAN,
2-(1,3-DIOXO-1,3-DIHYDRO-2H-ISOINDOL-2-YL)-5-OXO-5-(4-TOLUIDINO)PENTANOIC ACID,
4-[(2-TERT-BUTYL-(1H)-INDOL-5-YL)AMINO]-1-[(2-CHLOROPHENYL)CARBONYL]PIPERIDINE,
2-[(2-CHLOROBENZOYL)AMINO]-N-[2-(1H-INDOL-3-YL)ETHYL]BENZAMIDE,
5-(4-CHLOROANILINO)-2-(1,3-DIOXO-1,3-DIHYDRO-2H-ISOINDOL-2-YL)-5-OXOPENTANOIC ACID,
CARBOBENZYLOXY-L-METHIONYL-L-TRYP-TOPHAN,
CARBOBENZYLOXY-L-PHENYLALANYL-L-TRYP-TOPHANAMIDE,
N-ACETYL-5-BENZYLOXY-DL-TRYPTOPHAN, CAR-BOBENZYLOXYTRYPTOPHAN BETA-NAPHTHY-LAMIDE,
CARBOBENZYLOXYNORVALYLTRYP-TOPHANAMIDE, L-NORLEUCYL-L-TRYPTOPHAN,
CARBOBENZYLOXY-L-TRYPTOPHYL-L-PHENYLA-LANINAMIDE, CARBOBENZYLOXY-L-TRYPTO-PHYL-L-LEUCINAMIDE,
CARBOBENZYLOXY-L-TRYPTOPHYLGLYCYLGLY-CINE METHYL ESTER,
N-BETA-FMOC-L-BETA-HOMOTRYPTOPHAN
indane derivatives: for example
4-SULFOBENZOIC ACID (5-INDANYLMETHYLENE) HYDRAZIDE,
PHENYLINDANE DICARBOXYLIC ACID,
GLUTARIC ACID (5-INDANYLMETHYLENE)HY-DRAZIDE,
MALONIC ACID (5-INDANYLMETHYLENE)HY-DRAZIDE,
ADIPIC ACID (5-INDANYLMETHYLENE)HY-DRAZIDE,
5-(5-INDANYLMETHYLENEAMINO)SALICYLIC ACID,
FMOC-2-AMINOINDANE-2-CARBOXYLIC ACID;
Hippuric acid derivatives: for example
N-ALPHA-HIPPURYL-L-HISTIDYL-L-LEUCINE,
P-HYDROXYHIPPURYL-HIS-LEU-OH,
HIPPURYL-HIS-LEU ACETATE SALT,
HIPPURYL-ARG-GLY,
HIPPURYL-L-HISTIDYL-L-LEUCINE HYDRATE,
HIPPURYL-L-HISTIDYL-L-LEUCINE,
N-ALPHA-HIPPURYL-L-ARGININIC ACID HCL,
HIPPURYL-LYS-VAL-OH;
imidazole and benzimidazole derivatives: for example
N-(2-(2-PYRIDYL)-5-BENZIMIDAZOLYL)MALEAMIC ACID,
N-[2-(1H-BENZO[D]IMIDAZOL-2-YL)PHENYL]-N'-(4-METHOXYPHENYL)THIOUREA,
4-[4-(8-METHYLIMIDAZO[1,2-A]PYRIDIN-2-YL) ANILINO]-4-OXOBUTANOIC ACID, 4-[6-[2-(4-CARBOXYPHENYL)-1H-BENZO[D]IMIDAZOL-5-YL]-1H-BENZO[D]IMIDAZOL-2-YL]BEN,
2-[3-(5-CARBOXY-1H-BENZO[D]IMIDAZOL-2-YL) PHENYL]-1H-BENZO[D]IMIDAZOLE-5-CAR-BOXYL,
5-(PIPERIDINE-1-CARBONYL)-1H-IMIDAZOLE-4-CARBOXYLIC ACID (2-BZ-4-BR-PH)-AMIDE, 2-PHENYLTHIOMETHYL-1-(2,4-DICHLOROANILI-
NOCARBONYLMETHYL)-1H-BENZIMIDAZOLE,
3-[6-ETHYL-7-HYDROXY-3-(1-METHYL-1H-BENZO
[D]IMIDAZOLE-2-YL]-4-OXO-4H-CHROMEN-2-YL,
1-(3,4-DIMETHYLPHENYLAMINOCARBONYL-
METHYL)-2-(2-PHENYLVINYL)BENZIMIDAZOLE,
2-(2-PHENYLVINYL)-1-(4-TRIFLUOROMETHOX-
YPHENYLAMINOCARBONYLMETHYL)BENZIMI-
DAZOLE,
FMOC-L-ALA-4-[5-(2-AMINO)IMIDAZOYL];
quinoxaline derivatives: for example
2-(3-(BENZENESULFONYLCYANOMETHYL)QUI-
NOXALIN-2-YLOXY)-BENZOIC ACID;
pyridine derivatives: for example
4,4'-BIS(3-(3-PYRIDYL)UREIDO)DIPHENYL-
METHANE,
4,4'-METHYLENEBIS(1-PHENYL-3-(3-PYRIDYLM-
ETHYL)UREA),
1,1'-HEXAMETHYLENEBIS(3-(3-PYRIDYLMETHYL)
UREA),
4,4'-METHYLENEBIS(N-(2-PYRIDYLOXYCARBO-
NYL)ANILINE),
4,4'-METHYLENEBIS(N-(3-PYRIDYLOXYCARBO-
NYL)ANILINE),
4,4'-METHYLENEBIS(1-PHENYL-3-(4-PYRIDYLM-
ETHYL)UREA),
4-(3-(2-FLUOROPHENYL)UREIDO)BENZOIC ACID
(2-PYRIDYLMETHYLENE)HYDRAZIDE,
2-PHENYL-2-[2-(4-PYRIDYLCARBONYL)HYDRA-
ZONO]ACETIC ACID,
N1-[2-(2,4-DICHLOROPHENOXY)PHENYL]-N-2-(3-PY-
RIDYLMETHYL)ETHANEDIAMIDE,
N'-[(ANILINOCARBONYL)OXY]-3-[(PYRIDIN-2-YL-
SULFONYL)METHYL]BENZENECARBOXIMIDA-
MIDE,
N'-([[(2-CHLOROPYRIDIN-3-YL)AMINO]CARBONYL]
OXY)-3-[(PYRIDIN-2-YLSULFONYL)METHYL],
N1-(4-ISOPROPYLPHENYL)-2-[[4-(3-PYRIDYL)PYRI-
MIDIN-2-YL]THIO]ACETAMIDE,
2-[([2-[(4-METHYLPHENYL)THIO]-3-PYRIDYL]CAR-
BONYL)AMINO]ACETIC ACID,
2-([[2-(4-CHLOROPHENOXY)-3-PYRIDYL]CARBO-
NYL]AMINO)ACETIC ACID,
2-[([2-[(4-CHLOROPHENYL)THIO]-3-PYRIDYL]CAR-
BONYL)AMINO]ACETIC ACID,
N-(3-CHLOROPHENYL)-N'-[6-[(5-CHLORO-3-PY-
RIDYL)OXY]-3-PYRIDYL]UREA,
N-(2,6-DICHLOROBENZOYL)-N'-[6-(3-PYRIDY-
LOXY)-3-PYRIDYL]UREA,
ETHYL 2-[(5-CHLORO-3-PYRIDYL)OXY]-5-[[(3,4-
DICHLOROANILINO)CARBONYL]AMINO]BEN-
ZOATE,
N1-(3-PYRIDYLMETHYL)-2-[[(2-CHLOROANILINO)
CARBOTHIOYL]AMINO]BENZAMIDE,
N-[[6-(4-CHLOROPHENOXY)-3-PYRIDYL]CARBO-
NYL]-N'-(4-CHLOROPHENYL)UREA,
N-(2-CHLOROPHENYL)-N'-[5-(2-PHENYLETH-1-
YNYL)-3-PYRIDYL]UREA,
4-BENZYLAMINO-5-CYANO-6-(4-METHOXYPHE-
NYL)-2-(4-PYRIDYL)PYRIMIDINE,
N-(2-CHLOROPHENYL)-N'-[[5-(2-PHENYLETH-1-
YNYL)-3-PYRIDYL]-CARBONYL]THIOUREA,
N-(4-METHOXYPHENYL)-N'-[[5-(2-PHENYLETH-1-
YNYL)-3-PYRIDYL]-CARBONYL]THIOUREA,
FMOC-L-2-PYRIDYL-ALA,
N1-PHENYL-3-[2-(6-FLUORO-2-PYRIDYL)HYDRA-
ZONO]-2-HYDROXYIMINOBUTANAMIDE,
2-[([6-[(4-METHYLPHENYL)THIO]-3-PYRIDYL]
AMINO)CARBONYL]CYCLOPROPANE-1-CAR-
BOXYLIC ACID,
N'1-[3-(1H-PYRROL-1-YL)-2-PYRIDYL]-3,4-DICHLO-
ROBENZENE-1-SULFONOHYDRAZIDE,
4-(METHYLNITROSAMINO)-1-(3-PYRIDYL)-1-BUTA-
NYL BETA-D-GLUCURONIDE,
4-(2,4-DICHLOROPHENYL)-5-(2-PHENYL-1-DIAZ-
ENYL)-2-(3-PYRIDYL)-PYRIMIDINE;
coumarin derivatives: for example
N-EPSILON-CBZ-L-LYSINE 7-AMIDO-4-METHYL-
COUMARIN HYDROCHLORIDE,
7-METHOXYCOUMARIN-4-ACETYL-PRO-LEU, COU-
MARIN 6, COUMARIN 7, COUMARIN 138, COU-
MARIN 152, COUMARIN 314, COUMARIN 334, COU-
MARIN 337, COUMARIN 343;
flavone and flavonoid derivatives: for example
3'-BENZYLOXY-5,7-DIHYDROXY-3,4'-DIMETHOXY-
FLAVONE,
FLAVONE-3-DIPHOSPHATE,
3'-BENZYLOXY-5,7-DIHYDROXY-3,4'-DIMETHOXY-
FLAVONE;
pyrimidine derivatives: for example
3-[(4-CHLORO-6-METHYLPYRIMIDIN-2-YL)AMINO]-
2-[3-[(PHENYLTHIO)-METHYL]BENZOYL]ACRYL,
N-(4-CHLOROPHENYL)-N'-[3-[(2,5,6-TRICHLOROPY-
RIMIDIN-4-YL)AMINO]-PHENYL]UREA,
2-BENZOYLAMINO-3-(2'-4-METHYLPYRIMIDYL)-
AMINOPROPENOLYHYDRAZIDE-4-CHLOROBEN-
ZALDEHYDE,
2-BENZOYLAMINO-3-(2'-(4'-METHYLPYRIMIDYL)-
AMINOPROPENOLYHYDRAZIDE-4-BENZALDE-
HYDEHYDE,
2-BENZOYLAMINO-3-(2'-(4'-METHYLPYRIMIDYL)
AMINOPROPENOLYHYDRAZIDE-4-METHYLBEN-
ZALDEHYDE,
2-BENZOYLAMINO-3-(2'-(4'-METHYLPYRIMIDYL)
AMINOPROPENOLYHYDRAZIDE-4-METHOXY-
BENZALDEHYDE,
2-BENZOYLAMINO-3-(2'-(4'-METHYLPYRIMIDYL)-
AMINOPROPENOLYHYDRAZONE-4-FLUO-
ROBENZA,
3-((4-METHYLPYRIMIDYL)-2-AMINO)-2-BENZOY-
LAMINO ACRYLOYL HYDRAZIDE DIMETHY-
LAMINO,
4-[[4-[(4,6-DIMETHYLPYRIMIDIN-2-YL)OXY]PHE-
NYL]AMINO]-4-OXO-(2Z)BUTENOIC ACID,
4-[[4-[(4,6-DIMETHYLPYRIMIDIN-2-YL)THIO]PHE-
NYL]AMINO]-4-OXO-(2Z)BUTENOIC ACID,
(2-AMINO-5-(3-AMINO-4-CHLORO-PHENYL)-PYRI-
MIDIN-4-YLSULFANYL)ACETIC ACID,
2-HO-BENZOIC ACID (2-(5-ET-HO-ME-PYRIMIDINYL-
SULFANYL)-PHETHYLIDENE)HYDRAZIDE,
(4-(3-(4-MEO-PHENYL)-THIOUREIDO)-6-METHYLPY-
RIMIDIN-2-YLSULFANYL)ACETIC ACID,
4-(2,4-DICHLOROPHENYL)-2-PHENYL-5-(2-PHENYL-
1-DIAZENYL)PYRIMIDINE, N-(4-CHLOROPHE-
NYL)-N'-[(1,3-DIBENZYLHEXAHYDROPYRIMI-
DIN-5-YL)METHYL]UREA,
N-(2-CHLOROBENZYL)-N'-[(1,3-DIBENZYL-
HEXAHYDROPYRIMIDIN-5-YL)METHYL]UREA,
FMOC-2-AMINO-4-[(2-AMINO)PYRIMIDINYL]BU-
TANOIC ACID,
4-OXO-4-([2-[(5-PHENYLTHIENO[2,3-D]PYRIMIDIN-
4-YL)AMINO]-ETHYL]AMINO)BUTANOIC ACID;
Piperidine derivatives: for example
N,N'-(METHYLENEDI-4,1-PHENYLENE)BIS(3-ME-
THYL-1-PIPERIDINE CARBOXAMIDE),
N,N'-(METHYLENEDI-4,1-PHENYLENE)BIS(4-ME-
THYL-1-PIPERIDINE CARBOXAMIDE),
N-[[1-(3-CHLORO-2-CYANOPHENYL)-4-PIPERIDYL]
CARBONYL]-N'-(2,6-DICHLOROPHENYL)UREA, N4-(1-BENZYL-4-PIPERIDYL)-3-(2,6-DICHLOROPHE-
NYL)-5-METHYLISOXAZOLE-4-CARBOXAMIDE,
1,4-BIS(2-CARBOXYBENZOYL)PIPERAZINE,
5-(PIPERIDINE-1-CARBONYL)-1H-IMIDAZOLE-4-
CARBOXYLIC ACID (2-BZ-4-BR-PH)AMIDE,
FMOC-4-CARBOXYMETHYLPIPERAZINE,
4-FMOC-PIPERAZINE-1-YLACETIC ACID,
2-[[2-(4-METHYLPIPERAZINO)PHENYL]METHYL-
ENE]MALONIC ACID,
1-BOC-PIPERIDINE-4-FMOC-AMINO-4-CARBOXY-
LIC ACID,
5-[(4-CHLOROBENZOYL)AMINO]-2-(3,5-DIMETH-
YLPIPERIDINO)BENZOIC ACID,
4-CHLORO-N-[4-[4-(2-METHOXYPHENYL)PIPER-
AZINO]IBUTYL]BENZAMIDE, FMOC-L-ALA[3-(1-
N-PIPERAZINYL(4-N-BOC))];
Sarcosine derivatives: for example
CARBOBENZYLOXYSARCOSYL-L-ALANINE,
CARBOBENZYLOXYGLYCYLGLYCYLSARCOSINE;
Oxazole, oxadiazole and isooxazole derivatives: for example
N1-(3-CHLOROPHENYL)-5-(3-PHENYLISOXAZOL-5-
YL)-1H-PYRAZOLE-1-CARBOXAMIDE,
N1-[2-[3-(4-CHLOROPHENYL)-1,2,4-OXADIAZOL-5-
YL]PHENYL]-3,4-DICHLOROBENZAMIDE,
2-([2-[4-(1,3-OXAZOL-5-YL)ANILINO]-2-OXOETHYL]
THIO)ACETIC ACID,
N-(5-METHYLISOXAZOL-3-YL)-N'-[(5-PHENYL-1,3,4-
OXADIAZOL-2-YL)CARBONYL]UREA,
N'-([[(2-FLUOROBENZOYL)AMINO]CARBONYL]
OXY)-N-(5-METHYLISOXAZOL-3-YL)IMINOFOR-
MAMIDE,
N-[3-(2-CHLOROPHENYL)-5-METHYLISOXAZOL-4-
YL]-N'-(3,4-DIMETHOXYPHENETHYL)UREA,
N4-[2-CHLORO-5-(1-HYDROXYIMINOETHYL)PHE-
NYL]-3-(2-CHLOROPHENYL)-5-METHYLISOX-
AZOLE,
2,6-DICHLORO-N'-[([[3-(2,6-DICHLOROPHENYL)-5-
METHYLISOXAZOL-4-YL]AMINO]CARBONYL);
pyrazole, triazole and tetraazole derivatives: for example
1-(2,5-DICHLORO-4-SULFOPHENYL)-5-PYRA-
ZOLONE-3-CARBOXYLIC ACID,
CARBOXYPYRAZOLONE-2,5-DISULFONIC ACID,
N-[4-[(4-CHLOROPHENYL)SULFONYL]-3-METHYL-
2-THIENYL]-N'-(3-CYCLOPROPYL-1H-PYRAZOLE,
N1-(1,3,5-TRIMETHYL-1H-PYRAZOL-4-YL)-2-[[(4-
CHLOROANILINO)CARBONYL]AMINO]BENZA-
MIDE,
N-BENZOYL-N'-[3-CYCLOPROPYL-4-[2-(3,4-DICHLO-
ROPHENYL)DIAZ-1-ENYL]-1H-PYRAZOL-5-YL,
1,5,1',5'-TETRAPHENYL-1H, 1'H-(3,3')BIPYRAZOLYL,
2-[[1-(4-METHOXYPHENYL)-3-METHYL-1H-PYRA-
ZOL-5-YL]AMINO]BENZOIC ACID,
N1-[2-(1,3-DIPHENYL-1H-4-PYRAZOLYL)-1-(HY-
DRAZINOCARBONYL)VINYL]-2,4-DICHLO-
ROBENZAMIDE,
N1-[1-[(BENZYLAMINO)CARBONYL]-2-(1,3-DIPHE-
NYL-1H-PYRAZOL-4-YL)VINYL]BENZAMIDE,
1-(3-CHLOROPHENYL)-5-(4-CHLOROPHENYL)-1H-
PYRAZOLE-3-CARBOXYLIC ACID,
5-(4-CHLOROPHENYL)-1-(2,5-DICHLOROPHENYL)-
1H-PYRAZOLE-3-CARBOXYLIC ACID,
5-(2-CHLOROPHENYL)-1-(2,4-DICHLOROPHENYL)-
1H-PYRAZOLE-3-CARBOXYLIC ACID,
5-(2-CHLOROPHENYL)-1-(3-CHLOROPHENYL)-1H-
PYRAZOLE-3-CARBOXYLIC ACID,
5-(2-CHLOROPHENYL)-1-(4-CHLOROPHENYL)-1H-
PYRAZOLE-3-CARBOXYLIC ACID,
5-(2-CHLOROPHENYL)-1-(3,4-DICHLOROPHENYL)-
1H-PYRAZOLE-3-CARBOXYLIC ACID,
N,5-BIS(4-CHLOROPHENYL)-1-(2,5-DICHLOROPHE-
NYL)-1H-PYRAZOLE-3-CARBOXAMIDE,
1-(4-CHLOROPHENYL)-5-(3,4-DICHLOROPHENYL)-
1H-PYRAZOLE-3-CARBOXYLIC ACID,
1-(4-CHLOROPHENYL)-5-PHENYL-1H-PYRAZOLE-3-
CARBOXYLIC ACID,
1-(2,4-DICHLOROPHENYL)-5-PHENYL-1H-PYRA-
ZOLE-3-CARBOXYLIC ACID,
1-(4-METHYLPHENYL)-5-PHENYL-1H-PYRAZOLE-3-
CARBOXYLIC ACID,
1-(4-FLUOROPHENYL)-5-PHENYL-1H-PYRAZOLE-3-
CARBOXYLIC ACID,
5-(2-CHLOROPHENYL)-N-(3,4-D 1 METHYLPHENYL)-
1-PHENYL-1H-PYRAZOLE-3-CARBOXAMIDE,
1-(2-CHLOROPHENYL)-5-PHENYL-1-H-PYRAZOLE-
3-CARBOXYLIC ACID,
1-[2-(2,4-DICHLOROPHENOXY)PHENYL]-5-PHENYL-
1H-1,2,3-TRIAZOLE-4-CARBOXYLIC ACID,
1-BENZYL-3-[2-[(1-METHYL-5-CARBOXYTHI-
OMETHOXY)-1,3,4-TRIAZOLYL]]-2-PYRIDONE,
O-(2,4-DICHLOROBENZYL)-N-[1-PHENYL-1,2,4-
TRIAZOLE-3-OXYACETYL]FORMALDOXIME,
FMOC-L-TRANSPRO(4-TETRAZOYL);
thiazole and benzothiazole derivatives: for example
1,1'-(4-METHYL-1,3-PHENYLENE)BIS(3-(2-BEN-
ZOTHIAZOLYL)UREA), 4,4'-METHYLENEBIS(1-
PHENYL-3-(2-THIAZOLYL)UREA),
4-CHLORO-N'-[([[2-(2,3-DICHLOROPHENYL)-1,3-
THIAZOL-4-YL]AMINO]CARBONYL)OXY]BEN-
ZENE,
N-PHENYL-N-(4-CHLOROPHENYL)URIDO-3-(2-
ETHOXYCARBONYLPHENYL)-1-AMINO THIAZ-
OLE,
2-(2,5-DIHYDROXYPHENYLTHIO)BENZOTHIAZOLE-
5-SULFONIC ACID,
3-CARBOXYMETHYL-2-CARBOXYMETHYLSULFA-
NYL-BENZOTHIAZOL-3-IUM CHLORIDE,
3-[6-(2-CARBOXYETHYL)[1,3]THIAZOLO[5',4':4,5]
BENZO[D][1,3]THIAZOL-2-YL]PROPANOIC ACID,
2-(2-(4-CHLOROPHENYL)-4-PHENYLTHIAZOL-5-YL)
ACETIC ACID,
N-(2-BENZYLSULFANYLBENZOTHIAZOL-6-YL)
SUCCINAMIC ACID, 2-(2-[[2-(1,3-BENZOTHIAZOL-
2-YLSULFANYL)ACETYL]AMINO]-1,3-THIAZOL-
4-YL)ACETIC ACID;
triazine derivatives: for example
N1-[4-(BENZOYLAMINO)-1-PHENYL-6-(PHE-
NYLIMINO)-1,6-DIHYDRO-1,3,5-TRIAZIN-2-YL],
2-(3,5-DIOXO-2,3,4,5-TETRAHYDRO-(1 ,2,4)TRIAZIN-
6-YLAMINO)PENTANEDIOIC ACID,
O6-(4-CHLOROBENZOYL)-3,5-DIOXO-2-PHENYL-4-
PROPYL-2,3,4,5-TETRAHYDRO-1,2,4-TRIAZINE,
3-[3,5-DI(TERT-BUTYL)PHENYL]-N-(4-METHOXY-6-
METHYL-1,3,5-TRIAZIN-2-YL)-2,2-DIOXO;
morpholine derivatives: for example
4,4'-METHYLENEBIS(N-(2,6-DIMETHYLMORPHOLI-
NOCARBOXAMIDO)ANILINE), 1,1'-HEXAMETH-
YLENEBIS(3-(2-MORPHOLINOETHYL)UREA),
1,3-DIPHENYL-1-(2-MORPHOLINO-1-CYCLO-
PENTEN-1-YLCARBONYL)UREA,
N-(2-(4-DIMETHYLAMINOPHENYL)-1-(MORPHO-
LINE-4-CARBONYL)VINYL)BENZAMIDE,
METHYL 5-[[(3,5-DICHLOROANILINO)CARBONYL]
AMINO]-2-MORPHOLINOBENZOIC ACID,
FMOC-2-CARBOXYMORPHOLINE,
N-(2-MORPHOLINOETHYL)-4-OXO-4-[(2,3,6,7-TET-
RAHYDRO-(1H,5H)-BENZO[IJ]QUINOLIZINE;
Chromene derivatives: for example
2-([2-OXO-2-[(4-OXO-2-PHENYL-4H-CHROMEN-3-
YL)AMINO]ETHYL]THIO)ACETIC ACID, N1-(4-OXO-2-PHENYL-4H-CHROMEN-3-YL)-2-(ETHYLSULFONYL)ACETAMIDE,
2-OXO-2-[(4-OXO-2-PHENYL-4H-CHROMEN-3-YL)AMINO]ACETIC ACID;
pyrrole and dipyrrole, tripyrrole, and tetrapyrrole derivatives and organometallic compounds thereof, i.e., porphyrins and protoporphyrins: for example
3-[1-CYANO-3-(2-PHENYLHYDRAZONO)PROP-1-ENYL]-1-PHENYL-5-(1H-PYRROL-1-YL),
N'-([[(2,6-DICHLOROBENZOYL)AMINO]CARBONYL]OXY)-N-[2,5-DICHLORO-4-(1H-PYRROL-1-YL,
N-[4-(2,4-DICHLOROBENZOYL-2-PYRROLYL]-N'-PHENYLUREA,
O-(2,4-DICHLOROBENZYL)-N-[4-(2,4-DICHLOROBENZOYL)PYRROLE-2-CARBONYL]FORMAMIDOXIME,
5-(4-METHYLPHENYL)-2,3-DIHYDRO-1H-PYRROLIZINE-6,7-DICARBOXYLIC ACID, 5-PHENYL-2,3-DIHYDRO-1H-PYRROLIZINE-6,7-DICARBOXYLIC ACID,
5-(3-CHLOROPHENYL)-2,3-DIHYDRO-1H-PYRROLIZINE-6,7-DICARBOXYLIC ACID, 5-(4-CHLOROPHENYL)-2,3-DIHYDRO-1H-PYRROLIZINE-6,7-DICARBOXYLIC ACID, 5-(4-FLUOROPHENYL)-2,3-DIHYDRO-1H-PYRROLIZINE-6,7-DICARBOXYLIC ACID, 5-(4-METHOXYPHENYL)-2,3-DIHYDRO-1H-PYRROLIZINE-6,7-DICARBOXYLIC ACID,
3-PHENYL-PYRROLO(2,1,5-CD)INDOLIZINE-1,2-DICARBOXYLIC ACID,
1-(2-BENZO[1,3]DIOXOL-5-YL-ET)-2-(2-CARBOXY-ET)-OXOPYRROLIDINECARBOXYLIC ACID,
FMOC-4-AMINO-1-BOC-PYRROLIDINE-2-CARBOXYLIC ACID,
1-[(9H-FLUOREN-9-YLMETHOXY)CARBONYL]PYRROLIDINE-2-CARBOXYLIC ACID,
1-(TERT-BUTOXYCARBONYLAMINOETHYL)-2-METHYL-5-PHENYLPYRROLE-3-CARBOXYLIC ACID,
2-N'-FMOC-AMINOMETHYLPYRROLIDINE-N-ACETIC ACID,
3-N'-FMOC-AMINOPYRROLIDINE-N-ACETIC ACID,
(2S, 4RS)-4-FMOC-AMINO-1-BOC-PYRROLIDINE-2-CARBOXYLIC ACID, BILIRUBIN, HEMATIN;
trisubstituted, tetrasubstituted, pentasubstituted ethanoic or propanoic acid derivatives: for example
N-(2-HYDROXYETHYL)ETHYLENEDIAMINETRIACETIC ACID,
N-(2-HYDROXYETHYL)ETHYLENEDIAMINE-N,N',N'-TRIACETIC ACID,
ETHYLENEBIS(OXYETHYLENENITRILO)]TETRAACETIC ACID,
1,6-DIAMINOHEXANE-N,N,N',N'-TETRAACETIC ACID,
N-(2-HYDROXYETHYL)ETHYLENEDIAMINETRIACETIC ACID, ETHYLENEDIAMINETETRAACETIC ACID,
2-OXO-1,1,3,3-CYCLOHEXANETETRAPROPIONIC ACID,
N,N,N',N'-1,4-PHENYLENEDIAMINETETRAACETIC ACID,
ETHYLENE GLYCOL BIS(BETA-AMINOETHYL-ETHER)-N,N,N',N'-TETRAACETIC ACID,
ETHYLENEGLYCOL-BIS(BETA-AMINOETHYL-ETHER)-N,N,N',N'-TETRAACETIC ACID,
DIETHYLENETRIAMINEPENTMCETIC ACID;
stilbene derivatives: for example
2,3,5,4'-TETRAHYDROXYSTILBENE-2-O-BETA-D-GLUCOSIDE,
4,4'-DIHYDRAZINOSTILBENE-2-2'-DISULFONIC ACID,
4-ACETAMIDO-4'-ISOTHIOCYANATOSTILBENE-2,2'-DISULFONIC ACID;
Aromatic compounds substituted with 2-5 halogen atoms (Cl, Br or I): for example 1-(4-BENZOYLPHENYL)-3-(2,4-DICHLOROPHENYL)UREA,
N,N'-(4-(ALPHA-CYANO-2,4-DICHLOROSTYRYL)-1,2-PHENYLENE)BISACETAMIDE,
1-(2-BENZOYL-4-CHLOROPHENYL)-3-(2,5-DICHLOROPHENYL)UREA,
1-(4-BENZOYLPHENYL)-3-(2,5-DICHLOROPHENYL)UREA, 3',4'-DICHLOROPHTHALANILIC ACID, 1-(2-BENZOYL-4-CHLOROPHENYL)-3-(2,6-DICHLOROPHENYL)UREA, 1-(2-BENZOYL)-4-CHLOROPHENYL)-3-(2,3-DICHLOROPHENYL)UREA, 1-(2-CARBOXYPHENYL)-3-(2,3-DICHLOROPHENYL)UREA, 1-(2-CARBOXYPHENYL)-3-(3,4-DICHLOROPHENYL)UREA, 2-[(2-CARBOXY-4,6-DICHLOROPHENYL)THIO]-3,5-DICHLOROBENZOIC ACID, 4-[2-(2,4-DICHLOROPHENOXY)ANILINO]-4-OXOBUT-2-ENOIC ACID, 4-[2-(2,4-DICHLOROPHENOXY)ANILINO]-4-OXOBUTANOIC ACID, N-BENZOYL-N'-[2-(2,4-DICHLOROPHENOXY)PHENYL]THIOUREA, 3-[(3,5-DICHLOROANILINO)CARBONYL]PYRAZINE-2-CARBOXYLIC ACID, N1-(4-FLUOROPHENYL)-2-[[(3,4-DICHLOROANILINO)CARBOTHIOYL]AMINO]BENZAMIDE, N-[2-(2,4-DICHLOROPHENOXY)PHENYL]-N'-(2,6-DIFLUOROBENZOYL)UREA, N-(2-CHLORO-6-FLUOROBENZOYL)-N'-[2-(2,4-DICHLOROPHENOXY)PHENYL]UREA, N1-[2-[5-(3,4-DICHLOROPHENYL)-1,3,4-OXADIAZOL-2-YL]PHENYL]-3-METHYLBENZAMIDE, ETHYL 2-[(5-CHLORO-3-PYRIDYL)OXY]-5-[[(3,4-DICHLOROANILINO)CARBONYL]AMINO]BENZOIC ACID, N-[2-(?,4-DICHLOROPHENOXY)BENZOYL]-N'-(2,4-DIFLUOROPHENYL)UREA, N-[2-(2,4-DICHLOROPHENOXY)BENZOYL]-N'-(3,5-DICHLOROPHENYL)UREA, 3-[[(2,5-DICHLOROANILINO)CARBOTHIOYL]AMINO]PROPANOIC ACID, N1-(4-[[(3,4-DICHLOROANILINO)CARBOTHIOYL]AMINO]PHENYL)-2-HYDROXYBENZAMIDE, N1-(4-[[(2,3-DICHLOROANILINO)CARBOTHIOYL]AMINO]PHENYL)-2-HYDROXYBENZAMIDE, N1-(3-[[(3,4-DICHLOROANILINO)CARBOTHIOYL]AMINO]PHENYL)-2-HYDROXYBENZAMIDE, 1-(1-(3,4-DICHLOROBENZYL))-3-(2-METHOXYCARBONYLPHENYL)UREIDO-2-PYRIDONE,
1-(1-(3,4-DICHLOROBENZYL))-3-(3-ISOPROPOXYPHENYL)UREIDO-2-PYRIDONE,
BIS-(4-METHYLPHENYLAMINO)MALONAMIDE-2-(2,4-DICHLOROBENZYLOXIME)METHYLENE,
4-(3-(3-CHLOROPHENYL)UREIDO)BENZOIC ACID (3,4-DICHLOROBENZYLIDENE)HYDRAZIDE, 3-(N-(3,4-DICHLOROPHENYL)CARBAMOYL)-5-NORBORNENE-2-CARBOXYLIC ACID, 2-CARBOXYMETHYLTHIO-2',4'-DICHLORO-2-PHENYLACETANILIDE, O-(2,4-DICHLOROBENZYL)-N-[1-PHENYL-1,2,4-TRIAZOLE-3-OXYACETYL]FORMALDOXIME,
3,3-DICHLORO-2-(4-CHLOROBENZOYLAMINO)ACRYLIC ACID, 2-[[2-(3,5-DICHLOROANILINO)-2-OXOETHYL]THIO]NICOTINIC ACID, 1-[[(2,3-DICHLOROANILINO)CARBOTHIOYL]AMINO]ETHYLPHOSPHONIC ACID, 2-[[2-(2,4-DICHLORO-5-ISOPROPOXYANILINO)-2-OXOETHYL]SULFANYL] ACETIC ACID, 2-([2-[5-(BENZYLOXY)-2,4-DICHLOROAN ILINO]-2-OXOETHYL]SULFANYL) ACETIC ACID, 2-([2-[2,4-DICHLORO-5-(2-

PROPYNYLOXY)ANILINO]-2-OXOETHYL]SULFA-NYL)ACETIC ACID, 2,4-DICHLORO-N-[3-[(2,4-DICHLOROBENZOYL)AMINO]-3-OXOPROPANOYL]BENZENECARBOXAMIDE, FMOC-(R)-3-AMINO-4-(3,4-DICHLOROPHENYL) BUTYRIC ACID, FMOC-2,4-DICHLORO-L-PHENY-LALANINE, 1-(2-BENZOYL-4-CHLOROPHENYL)-3-(2,4,5-TRICHLOROPHENYL)UREA, 3-(3-(2,4,5-TRICHLOROPHENYL)UREIDO)BENZOIC ACID, N1-(4-FLUOROPHENYL)-2-(BENZOYLAMINO)-3,5-DIBROMOBENZAMIDE, 2,3,5-TRIIODOBENZOIC ACID, IOPHENOXIC ACID;

Dyes from the class of azo dyes: for example P-PHENYLA-ZOMALEANILIC ACID, 2-(2-PYRIDYLAZO)CHRO-MOTROPIC ACID, 2,2'-AZOXYDIBENZOIC ACID, 4-(1,8-DI HYDROXY-3,6-DISULFO-2-NAPHTHY-LAZO)SALICYLIC ACID, 3-(2-(2,5-DICHLOROBE-NYLAZO)-5-(DIETHYLAMINO)-PHENYLCARBAM-OYL)PROPIONIC ACID, 1-(4-(METHYLTHIO) PHENYL)-3-(4-(PHENYLAZO)PHENYL)UREA, 2-HO-5-(4'-HO-BIPHENYL-4-YLAZO)BENZOIC ACID, PYRIDYL-2-AZOCHROMOTROPIC ACID, SULFONAZO III, BRILLIANT CROCEIN MOO (=ACID RED 73), TROPAEOLIN (=ACID ORANGE 6), CHICAGO BLUE 6B, BORDEAUX R, ERIOCHROME BLACK, ACID RED 151, DISPERSE YELLOW 7, PON-CEAU SS, DIMETHYLAMINO-1-NAPHTHYLAZO-4-METHOXYBENZENESULFONIC ACID, SUDAN II ACID RED 88, MORDANT BROWN 1, TRYPAN BLUE (=DIRECT BLUE 14), EVANS BLUE, ACID ORANGE 8, SUDAN IV, MORDANT BROWN 33, DIRECT YELLOW 50, HABA (=2-(4'-HYDROXYBEN-ZENEAZO)BENZOIC ACID), CONGO RED, 8-HY-DROXY-7-(4-SULFOLNAPHTHYLAZA)-5-QUINO-LINIC ACID, SULFANILAZOCHROMOTROPE, NAPHTHOL BLACK, NITRO RED, XYLIDINE PON-CEAU, ORANGE G, MORDANT YELLOW 10, BEN-ZOPURPURIN 4B, CROCEIN ORANGE G, METANIL YELLOW, DIRECT RED 81;

Dyes from the class of anthraquinones: for example ALIZARIN COMPLEXON (=N-(3,4-DIHYDROXY-2-ANTHRAQUINONYLMETHYLIMINODIACETIC ACID), ALIZARIN, REMAZOL BRILLIANT BLUE R, ALIZARIN YELLOW GG, ALIZARIN RED S, ALIZARIN BLUE BLACK B, NUCLEAR FAST RED;

Dyes from the class of phthaleins and sulfophthaleins: for example BROMCRESOL GREEN, TETRAIODOPHENOLPHTHALEIN, TETRABRO-MOPHENOLSULFONEPHTHALEIN, BRO-MCRESOLLIA, THYMOL BLUE, BROMTHYMOL BLUE, CRESOL RED, IODOPHENOL BLUE (=TET-RAIODOPHENOLSULFONEPHTHALEIN), BROMO-CHLOROPHENOL BLUE,

TETRABROMOPHENOL BLUE, BROMOPYRO-GALLOL RED,

COOMASSIE BRILLIANT BLUE R250, CHLOROPHE-NOL RED, XYLENOL BLUE, ACID VIOLET 17;

dipeptides, tripeptides, tetrapeptides, pentapeptides and hexapeptides, that may be substituted by Z (=benzyloxy-carbonyl), BOC (N-tert-butoxycarbonyl), FMOC (N-9-fluorenylmethoxycarbonyl), Ac (=acetyl) or CBZ (=car-bobenzyloxy): for example Z-TYR-TYR-OH, Z-VAL-ALA-OH, Z-ILE-ALA-OH, AC-ALA-ALA-ALA-ALA-OH (SEQ ID NO:14), Z-VAL-PHE-OH, Z-MET-PHE-OH, DL-LEUCYL-GLYCYL-DL-PHENYLALANINE, Z-PRO-D-LEU-OH, CARBOBENZYLOXY-L-VA-LYLGLYCYLGLYCINE, Z-LEU-GLY-GLY-OH, Z-ALA-GLY-GLY-OH, Z-ALA-TRP-GLY-OH, CARBOBEN-ZYLOXY-L-METHIONYL-L-TRYPTOPHAN, CAR-BOBENZYLOXY-L-PHENYLALANYL-L-TRYP-TOPHANAMIDE, CARBOBENZYLOXY-L-ISOLEUCYL-L-PHENYLALANINAMIDE, Z-PHE-MET-OH, Z-VAL-MET-OH, Z-LEU-MET-OH, CARBOBENZYLOXY-L-NORVALYL-L-LEUCINE, H-GLY-LEU-GLY-LEU-OH (SEQ ID NO:15), Z-ILE-ILE-OH, Z-PHE-ILE-OH, Z-NVA-NVA-OH, N-ALPHA-Z-L-ARGININE HYDROBROMIDE, N-FORMYL-MET-LEU-PHE, FMOC-ASN-OH, H-PHE-ARG-OH, ARG-ILE, H-PHE-TYR-OH, Z-PHE-TYR, Z-GLU-TYR-OH, TYR-LEU, H-GLU(TYR)-OH, Z-LEU-ALA-OH, Z-TYR-ALA-OH, Z-PHE-ALA-OH, Z-GLY-ALA-OH, Z-GLY-GLY-ALA-OH, H-TYR-PHE-OH, PHE-PHE-PHE, Z-GLU-PHE-OH, Z-GLY-PHE-OH, H-GLU-GLY-PHE-OH, Z-LEU-GLY-OH, H-PHE-ASP-OH, H-ARG-ASP-OH, Z-GLY-ASP-OH, TYR-GLU, H-ARG-GLU-OH, H-GLU-ASP-OH, GLU-GLU, H-GLU-GLU-GLU-OH, Z-ALA-PRO-OH, Z-PHE-PRO-OH, Z-PHE-GLY-OH, H-PHE-GLY-GLY-OH, TYR-GLY-GLY, Z-GLY-GLY-GLY-OH, Z-THR-PHE-OH, Z-TYR-THR-OH, Z-ORN(Z)-OH, Z-HIS-PHE-OH, H-PRO-VAL-ASP-OH, PYR-ASN-GLY-OH, Z-TRP-ALA-OH, H-LEU-TRP-LEU-OH, H-MET-TRP-OH, H-GLU-TRP-OH, H-ARG-TRP-OH, H-LYS-TRP-OH, AC-PHE-TRP-OH, H-TRP-TRP-OH, H-TRP-SER-OH, TRP-PHE, H-TRP-TYR-OH, H-TRP-LEU-OH, H-TRP-GLU-OH, H-ALA-PHE-GLY-OH, H-GLY-GLY-MET-OH, H-GLY-GLY-GLU-OH, ARG-LYS, H-LYS-GLU-OH, H-LYS-TYR-GLU-OH, H-LYS-GLU-GLY-OH, H-LYS-LYS-LYS-OH, Z-LEU-LEU-OH, Z-ALA-LEU-OH, Z-TYR-LEU-OH, Z-PHE-LEU-OH, Z-GLY-GLY-LEU-OH, H-DL-ALA-DL-LEU-GLY-OH, H-MET-PHE-GLY-OH, H-GLU-TYR-GLU-OH, H-MET-ARG-PHE-OH, H-PHE-ILE-OH, H-LEU-TRP-MET-OH, N-FORMYL-MET-PHE-MET, L-GLN-L-GLN-L-GLN, Z-ARG-OH HCL, H-ARG-ARG-OH ACOH, H-ALA-ARG-OH, Z-GLY-HIS-OH, N-ACETYL-5-BENZYLOXY-DL-TRYPTOPHAN, Z-GLY-TRP-OH, H-TRP-ILE-OH, LEU-ARG, Z-GLY-TYR-OH, CARBOBENZYLOXY-BETA-ALANYL-L-ALANINE, Z-GLY-GLY-SER-OH, MET-LEU-PHE, Z-GLY-GLY-PHE-OH, CARBOBEN-ZYLOXY-BETA-ALANYL-L-PHENYLALANINE, Z-GLY-GLY-NLE-OH, H-ARG-ASP-OH, Z-ALA-GLU-OH, Z-GLY-GLY-PRO-OH, Z-ILE-GLY-GLY-OH, Z-BETA-ALA-GLY-GLY-OH, H-GLU-LYS-OH, Z-GLY-GLY-MET-OH, Z-GLY-GLY-ILE-OH, N-CBZ-BETA-ALA-BETA-ALA, N-ACETYL-MET-LEU-PHE, GLU-VAL-PHE, S-DECYLGLUTATHIONE, S-PROPYLGLUTATHIONE, S-BUTYLGLU-TATHIONE, S-HEXYLGLUTATHIONE, S-OCTYL-GLUTATHIONE, S-(P-CHLOROPHENACYL) GLU-TATHIONE, S-(P-AZIDOPHENYLACYL)-GLUTATHIONE, Z-PRO-LEU-GLY-OH, Z-PRO-LEU-GLY-NH2, N-FORMYL-NLE-LEU-PHE, GLY-PHE-ARG, BOC-PHE-PHE-GLY-OH, H-ASP-GLU-OH, H-TYR-TYR-PHE-OH, H-GAMMA-GLU-TRP-OH, GLUTATHIONE SULFONIC ACID, H-ASP-GLN-OH, H-ARG-GLY-ASP-OH, H-LYS-LYS-OH 2 HCL, ARG-SER-ARG, Z-ALA-PRO-TYR-OH, AC-PHE-TYR-OH, H-TYR-TYR-OH, H-ASP-PHE-OH, N-CARBOBEN-ZOXYGLYCYL-DL-PHENYLALANINE, H-GLU-TYR-OH, S-ETHYLGLUTATHIONE, H-ALA-ALA-ALA-ALA-OH (SEQ ID NO:16), H-ARG-LYS-OH, Z-VAL-LEU-OH, H-ARG-ARG-OH, N-FORMYL-NLE-LEU-PHE-OH, H-TYR-GLY-GLY-PHE-OH (SEQ ID NO:17), ALA-GLY-SER-GLU (SEQ ID NO:18), VAL-GLY-SER-GLU, H-ARG-GLY-ASP-ALA-OH (SEQ ID NO:19), H-ARG-GLY-ASP-CYS-OH (SEQ ID NO:20), H-ARG-GLY-ASP-SER-OH (SEQ ID NO:21), ARG-GLY-GLU-SER (SEQ ID NO:22), H-ARG-GLY-ASP-VAL-OH (SEQ ID NO:23), H-GLY-ARG-GLY-ASP-OH (SEQ ID NO:24), H-LYS-GLY-ASP-SER-OH (SEQ ID NO:25), AC-ASP-GLU-OH, H-GLY-GLY-TYR-ARG-OH (SEQ ID NO:26), AC-SER-ASP-LYS-PRO-OH (SEQ ID NO:27), Z-GLY-GLY-GLY-GLY-GLY-OH (SEQ ID NO:28), H-ALA-GLY-GLY-GLY-GLY-OH (SEQ ID NO:29), H-LYS-TYR-LYS-OH, H-D-TYR-TRP-GLY-OH, BOC-ALA-GLY-GLY-OH, GLU-ALA-GLU, LYS-TYR-LYS, SER-ASP-GLY-ARG (SEQ ID NO:30), AC-TYR-VAL-GLY, BZ-GLY-ALA-PRO, Z-GLY-PRO-LEU, Z-GLY-PRO-LEU GLY (SEQ ID NO:31), Z-TYR-GLU-OH, H-ALA-ALA-TYR-ALA-ALA-OH (SEQ ID NO:32), SUC-ALA-ALA-ALA-4M-BETA-NA, H-ARG-TRP-OH SALT, H-ARG-TYR-OH SALT, H-ASP-ARG-BETA-NA, H-LYS-PHE-TYR-OH, Z-PRO-LEU-GLY-NHOH, H-GLY-GLY-ARG-ALA-OH (SEQ ID NO:33), H-GLY-GLY-GLU-ALA-OH (SEQ ID NO:34), H-GLY-GLY-GLY-GLY-GLY-OH (SEQ ID NO:35), H-GLY-GLY-GLY-GLY-GLY-GLY (SEQ ID NO:36), H-ILE-ARG-OH, H-LYS-THR-TYR-OH, H-LYS-TYR-SER-OH, H-MET-ARG-OH, PHE-GLY-GLY-PHE (SEQ ID NO:37), H-PHE-TRP-OH, H-TYR-LYS-OH, H-TYR-TRP-OH, VAL-ALA-ALA-PHE, CARBOBENZYLOXYALANYLMETHIONINE, CARBOBENZYLOXYGLYCYLGLYCYLSARCOSINE, CARBOBENZYLOXYISOLEUCYLMETHIONINE, CARBOBENZYLOXYGLYCYLLEUCYLGLYCINE BENZYL ESTER, CARBOBENZYLOXYTRYPTOPHAN BETA-NAPHTHYLAMIDE, N-BENZYLGLYCYLGLYCYLPHENYLALANINE, CARBOBENZYLOXYNORVALYLTRYPTOPHANAMIDE, CARBOBENZYLOXYPHENYLALANYLGLYCYLGLYCINE METHYL ESTER, GLU-ALA-GLU-ASN (SEQ ID NO:38), GLY-ARG-GLY-ASP (SEQ ID NO:39), GLY-PRO-GLY-GLY (SEQ ID NO:40), H-MET-GLY-MET-MET-OH (SEQ ID NO:41), N-ACETYL-BETA-ASP-GLU, N-FORMYL-ALA-GLY-SER-GLU, SUC-ALA-ALA-VAL-OH, BOC-ALA-GLY-GLY-GLY-OH (SEQ ID NO:42), ORN-ORN-ORN, PHE-GLY-PHE-GLY (SEQ ID NO:43), PRO-THR-PRO-SER (SEQ ID NO:44), VAL-GLY-ASP-GLU (SEQ ID NO:45), VAL-THR-LYS-GLY (SEQ ID NO:46), AC-MET-ALA-SER-OH, AC-PRO-LEU-GLY-OH, BOC-PHE-GLY-OH, Z-TYR-LEU-NH2, H-VAL-VAL-GLY-OH, AC-D-PHE-TYR-OH, Z-HIS-TYR-OH, CARBOBENZYLOXY-L-TRYPTOPHYL-L-PHENYLALANINAMIDE, CARBOBENZYLOXY-L-TYROSYL-L-ALANINAMIDE, CARBOBENZYLOXY-L-SERYL-L-PHENYLALANINE, CARBOBENZYLOXY-L-PHENYLALANYLGLYCYLGLYCINAMIDE, CARBOBENZYLOXYGLYCYLGLYCYL-L-THREONINE, H-GLY-GLY-GLY-GLY-ALA-OH (SEQ ID NO:47), Z-DL-GLU-OH, Z-HIS-GLY-OH, CARBOBENZYLOXY-L-HISTIDYLGLYCYLGLYCINE, CARBOBENZYLOXY-L-TYROSYL-L-THREONINAMIDE, Z-TRP-GLY-OH, Z-TYR-VAL-OH, CARBOBENZYLOXY-L-HISTIDYL-L-TYROSINAMIDE, CARBOBENZYLOXY-S-BENZYL-L-CYSTEINYL-L-LEUCINAMIDE, N,N'-BIS(CARBOBENZYLOXY)-L-LYSYLGLYCINAMIDE, CARBOBENZYLOXY-L-TRYPTOPHYL-L-LEUCINAMIDE, Z-TYR-PHE-OH, CARBOBENZYLOXY-L-ISOLEUCYL-L-TYROSINAMIDE, Z-TRP-PHE-OH, CARBOBENZYLOXY-L-TRYPTOPHYLGLYCYLGLYCINE METHYL ESTER, CARBOBENZYLOXY-L-SERYL-L-TYROSINE, CARBOBENZYLOXY-L-TYROSYLGLYCINE, Z-GLY-D-TRP-OH, H-TYR-TYR-OH, BOC-D-GLN(XAN)-OH, H-ASP-ASP-ASP-OH, H-ASP-ASP-ASP-ASP-OH (SEQ ID NO:48), H-ASP-ALA-SER-VAL-OH (SEQ ID NO:49), H-MET-LEU-PHE-OH ACOH, H-D-TYR-GLU-GLY-OH, H-D-TYR-PHE-GLY-OH ACOH, H-TYR-THR-OH, H-D-TYR-TRP-GLY-OH ACOH, Z-ALA-TYR(BZL)-OH, Z-GLY-HIS-OH, Z-PHE-GLY-GLY-OH, GLYCYLGLYCYLGLYCYLGLYCYLGLYCYLALANINE (SEQ ID NO:50), TRH-GLY, VAL-THR-CYS-GLY (SEQ ID NO:51), H-ARG-GLU-OH, H-GLY-GLY-GLY-GLY-GLY-GLY-OH (SEQ ID NO:36), H-TRP-PHE-OH, H-TYR-GLU-OH, H-ARG-TYR-OH, BOC-GLY-ASP-OH, BOC-PHE-GLY-GLY-OH, FMOC-ALA-ALA-OH, FMOC-ALA-GLY-OH, FMOC-ALA-PRO-OH, FMOC-GLY-GLY-GLY-OH, FMOC-GLY-PHE-OH, FMOC-GLY-PRO-OH, FMOC-GLY-VAL-OH, FOR-VAL-PHE-GLY-OH, H-LEU-LEU-GLY-OH, H-LYS-ARG-OH, H-MET-GLY-GLY-OH, H-MET-HIS-OH, H-PHE-ARG-OH HBR, H-PRO-VAL-GLY-OH, H-TRP-ASP-OH, H-TYR-GLY-GLY-OH, H-TYR-ILE-OH, H-TYR-LEU-OH, Z-ALA-ARG-OH, Z-ALA-ASP-OH, Z-GLU-LEU-OH, Z-GLU-VAL-OH, Z-GLY-GLU-OH, Z-GLY-GLY-TRP-OH, Z-GLY-GLY-TYR-OH, Z-HIS-ALA-OH, Z-HIS-TRP-OH, Z-ILE-SER-OH, Z-DL-LEU-DL-ALA-OH, Z-LEU-D-ALA-OH, Z-LEU-BETA-ALA-OH, Z-LEU-PHE-OH, Z-LEU-PRO-OH, Z-LEU-SER-OH, Z-PHE-PHE-OH, Z-PHE-TRP-OH, Z-PHE-VAL-OH, Z-PRO-BETA-ALA-OH, Z-SER-GLY-OH, Z-TRP-LEU-OH, Z-VAL-VAL-OH, AC-LYS(AC)-D-ALA-D-ALA-OH, AC-LYS(AC)-D-ALA-D-LYS-OH, AC-LYS(AC)-D-GLU-D-ALA-OH, H-D-GLU-D-GLU-OH, H-D-PHE-D-PHE-OH, H-D-VAL-D-VAL-D-VAL-D-VAL-OH (SEQ ID NO:52), AC-HIS-GLY-HIS-OH, AC-HIS-PRO-PHE-OH, AC-HIS-SER-PHE-OH, AC-TYR-TYR-OH, BOC-GAMMA-GLU-LYS-OH, BOC-GLY-GLY-GLY-LYS-OH (SEQ ID NO:53), BOC-PHE-GLY-GLY-GLY-OH (SEQ ID NO:54), FMOC-ILE-PRO-OH, FMOC-NLE-NLE-OH, FMOC-PRO-PRO-OH, FMOC-VAL-PRO-OH, FOR-MET-LEU-GLU-OH, GLUTARYL-GLY-PHE-4M-BETA-NA, GLUTARYL-PHE-BETA-NA, H-ALA-ALA-ALA-ALA-D-GLU-OH (SEQ ID NO:55), H-ALA-ALA-ALA-ALA-GLU-OH (SEQ ID NO:56), H-ALA-ALA-ALA-TYR-ALA-OH (SEQ ID NO:57), H-ALA-ALA-PRO-ALA-ALA-OH (SEQ ID NO:58), H-ALA-ALA-TYR-ALA-OH (SEQ ID NO:59), H-ARG-GLN-OH, H-ARG-GLY-GLY-OH, H-ARG-ILE-OH, H-ARG-PHE-ALA-OH, H-ARG-SER-ARG-OH, H-ASN-GLU-OH, H-ASP-ALA-HIS-LYS-OH (SEQ ID NO:60), H-ASP-ALA-SER-GLY-GLU-OH (SEQ ID NO:61), H-ASP-ASN-GLN-OH, H-ASP-TRP-OH, H-CIT-PHE-OH, H-D-ARG-PHE-OH, H-D-GLU-GLU-OH, H-D-PHE-SER(BZL)-PHE-OH, H-GAMMA-GLU-GAMMA-GLU-GLN-OH, H-GAMMA-GLU-GAMMA-GLU-GLU-OH, H-GAMMA-GLU-GAMMA-GLU-LYS-OH, H-GLN-TRP-GLU-OH, H-GLU-GLU-ASP-OH, H-GLU-GLU-BETA-NA, H-GLU-GLU-LEU-OH, H-GLU-HIS-GLY-OH, H-GLU-PHE-TYR-OH, H-GLU-PRO-GLU-THR-OH (SEQ ID NO:62), H-GLU-SER-LEU-PHE-OH (SEQ ID NO:63), H-GLY-GLY-ARG-ANILIDE, H-GLY-GLY-GLY-BETA-ALA-OH, H-GLY-GLY-LYS-ALA-ALA-OH (SEQ ID NO:64), H-GLY-GLY-TYR-ALA-OH (SEQ ID NO:65), H-GLY-LEU-BETA-ALA-OH, H-GLY-LEU-DELTA-AMINOVALERIC ACID, H-GLY-LEU-LEU-GLY-OH (SEQ ID NO:66), H-GLY-LYS-GLY-OH, H-GLY-LYS-HIS-OH, H-HIS-TRP-LYS-OH, H-ILE-ARG-PRO-OH, H-ILE-GLN-OH, H-LEU-LEU-VAL-PHE-OH (SEQ ID NO:67), H-LEU-PHE-LEU-OH, H-LYS-ALA-PHE-GLY-OH (SEQ ID NO:68), H-LYS-ARG-OH, H-LYS-GLY-GLU-OH, H-LYS-GLY-GLY-LYS-OH (SEQ ID NO:69), H-LYS-GLY-LYS-OH, H-LYS-LEU-LYS-OH, H-LYS-PHE-LYS-OH, H-LYS-PRO-ARG-OH, H-LYS-PRO-ASN-OH, H-LYS-SER-LYS-OH, H-LYS-TYR-THR-OH, H-MET-ASP-GLY-OH, H-MET-GLN-OH, H-MET-LEU-GLY-OH, H-MET-SER-GLY-OH, H-MET-TRP-GLY-OH, H-MET-TYR- LYS-OH, H-ORN-ORN-ORN-OH, H-PHE-ARG-ARG-OH, H-PHE-GLN-GLY-PRO-OH (SEQ ID NO:70), H-PHE-TRP-NH2, H-PRO-GLU-THR-OH, H-PRO-HIS-GLU-OH, H-PRO-LEU-GLY-GLY-OH (SEQ ID NO:71), H-PRO-PHE-LYS-OH, H-SER-GLU-GLY-OH, H-SER-TYR-LYS-OH, H-THR-TYR-LYS-OH, H-THR-TYR-SER-LYS-OH (SEQ ID NO:72), H-TRP-ARG-OH, H-TRP-GLU-TYR-OH, H-TRP-GLY-GLY-TYR-OH (SEQ ID NO:73), H-TRP-MET-OH, H-TRP-PRO-TYR-OH, H-TYR-ARG-PRO-NH2, H-TYR-ARG-THR-NH2, H-TYR-GLN-OH, H-TYR-GLU-TRP-OH, H-TYR-LYS-TRP-OH, H-TYR-TYR-LEU-NH2, H-TYR-TYR-LEU-OH, H-VAL-ARG-OH, L-BETA-PHENYLLACTYL-GLN-TYR-OH, L-BETA-PHENYLLACTYL-GLY-TYR-OH, L-BETA-PHENYLLACTYL-PHE-TYR-OH, Z-ALA-ALA-LYS-OH, Z-ALA-PRO-GLY-OH, Z-ALA-PRO-LEU-OH, Z-ASP-MET-OH, Z-D-ALA-PHE-OH, Z-D-GLU-TYR-OH, Z-DL-LEU-GLY-OH, Z-GLU-MET-OH, Z-GLY-ALA-ALA-OH, Z-GLY-GLN-OH, Z-GLY-GLY-GLY-GLY-GLY-GLY-OH (SEQ ID NO:74), Z-GLY-GLY-HIS-OH, Z-GLY-ILE-ALA-OH, Z-GLY-LEU-ALA-OH, Z-GLY-LEU-GLY-OH, Z-GLY-PHE-ALA-OH, Z-GLY-PRO-ALA-OH, Z-GLY-PRO-GLY-GLY-OME (SEQ ID NO:75), Z-HIS-MET-OH, Z-ILE-HIS-OH, Z-LYS(Z)-ALA-OH, Z-LYS(Z)-GLY-OH, Z-LYS-LEU-OH, Z-PHE-ASP-OH, Z-PHE-GLU-OH, Z-PHE-LEU-ALA-OH, Z-TRP-MET-OH, Z-TRP-VAL-OH, Z-TYR-ILE-OH, Z-VAL-GLY-PHE-OH, Z-VAL-TRP-OH, GLY-GLY-L-PHE-L-MET (SEQ ID NO:76), L-TRP-TRP, L-TRP-TYR, Z-TYR-GLY-GLY-OH, H-MET-ASP-PHE-NH2, Z-GLY-ARG-OH, Z-ILE-GLU-OH, Z-LEU-D-PHE-OH, Z-PYR-HIS-OH, Z-LEU-GLU-OH, L-ARG-PHE-ALA, L-ARG-ARG, L-ASP-L-ARG, L-ALA-ALA-ALA-L-PRO-L-ALA-ALA (SEQ ID NO:77), L-ALA-LEU-ALA-GLY (SEQ ID NO:78), L-ARG-PRO-PRO, N-ACETYL-D-TRP-D-TRP, N-BENZOYL-L-ARG-PHE-ALA, CBZ-DL-PHE-GLY-GLY HYDRAZIDE, CBZ-L-ARG-PHE, CBZ-L-ALPHA-ASP-GLU, CBZ-GLY-GLY-L-ARG, CBZ-L-GLU-TRP, CBZ-D-ALA-L-ALA, CBZ-L-ALA-D-LEU, CBZ-D-LEU-L-ALA, CBZ-L-LEU-D-LEU, CBZ-L-VAL-D-LEU, CBZ-D-VAL-D-LEU, CBZ-L-VAL-D-PHE, GLY-ALA-ALA-D-ALA-L-ALA (SEQ ID NO:79), ALPHA-L-GLU-L-TRP-L-GLU, GAMMA-L-GLU-GAMMA-L-GLU-L-ALA, L-LYS-L-TRP OH, L-LEU-TRP-MET, L-LEU-TRP-LEU, L-LYS-TYR-LYS, L-PHE-L-ARG, L-PRO-PHE-ARG, L-PHE-D-PHE, L-SER-GLY-ALA-GLY-ALA-GLY (SEQ ID NO:80), L-TYR-L-MET, L-TRP-GLY-GLY-TYR (SEQ ID NO:81), D-TRP-D-TRP, L-TYR-TYR, H-THR-ARG-OH, FMOC-PHE-GLY-OH, FMOC-D-CIS-HYP-OH, FMOC-D-ALLO-THR-OH, FMOC-ALLO-THR-OH, FMOC-D-ASP-OH, PYR-TRP-GLY-NH2, H-PHE-PRO-ARG-OH, BOC-GLY-GLY-GLY-GLY-OH (SEQ ID NO:82), Z-PHE-GLY-OH, FMOC-ALA-ALA-PRO-OH, BOC-GLY-PRO-GLY-OH.

Therefore ligand compounds according to the invention comprise at least one therapeutically and/or diagnostically active substance and one carrier-molecule-affinitive substance, such as for example a protein-affinitive ligand, between the two of which a spacer molecule may be located. Thus ligand compounds according to the invention have the following general structures:

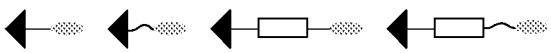

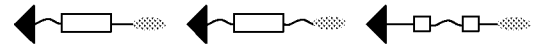

◀ = ligand    ░░░ = therapeutic or diagnostic agent

▭ = spacer molecule    ── = bond not cleavable in the body

∼ = pH-dependent or enzymatically cleavable in the body

◖◀ where log $K_A > 3$    ◖ = transport protein

For the example of Evans blue and bromcresol, which both have a high affinity for albumin, the structure of the ligand system according to the invention is schematically represented as:

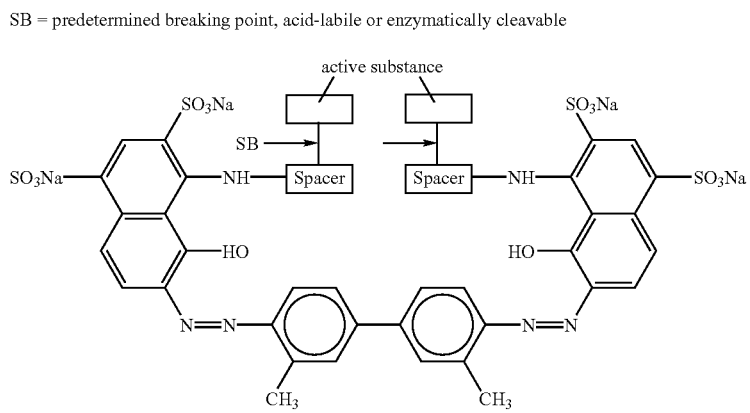

-continued
general structure of a protein-affinitive ligand system with Evans blue

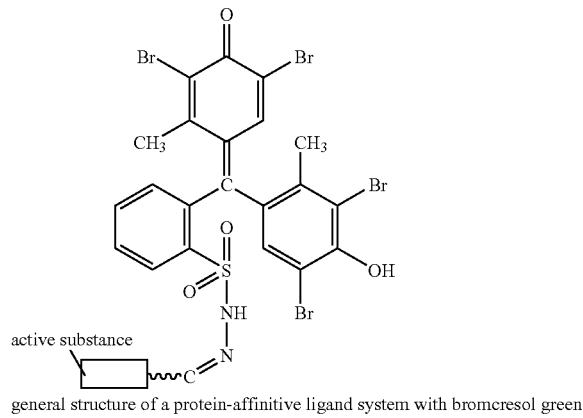

general structure of a protein-affinitive ligand system with bromcresol green

Surprisingly, by providing the ligand compound according to the invention, carrier-molecule-affinitive substances such as, for example, the above-indicated ligands of transport proteins that enter into a strong noncovalent interaction therewith in the bloodstream, can be used therapeutically and/or diagnostically by covalently bonding therapeutically and/or diagnostically active substances to such carrier-molecule-affinitive substances. Since such ligand systems bind to the carrier molecule, for example a transport protein, via the carrier-molecule-affinitive ligand, for example, a protein-affinitive ligand, the therapeutic or diagnostic agents bound to the ligand in this way are transported to their target site or their target cells or to pathogenic tissue, such as for example tissue having malignant-degenerated cells. According to the invention, an acid-labile or enzymatically cleavable bond between the active substance and the protein-affinitive ligand or spacer ensures that the active substance is released at the intracellular or extracellular site of action.

Thus, the ligand compound according to the invention provides a novel and superior prodrug concept, since the ligand compound according to the invention is transported to the site of action via the carrier-molecule-affinitive substance, which enters into a strong physical interaction with the carrier molecule, for example a serum protein such as albumin, and accumulates at that site. The ligand compound according to the invention also has excellent solubility in the medium at the site of action. Furthermore, the ligand compound according to the invention has the advantage that for preparation of the conjugate with the carrier molecule, the carrier molecule is not covalently modified since the interaction between the carrier-molecule-affinitive substance and the carrier molecule is of a physical nature. In preparation of such conjugates, therefore, a large number of process steps that are usually necessary are cancelled, which results in considerable savings of time and material and thus considerable cost reduction. This is also the case because the ligand compound does not have to be linked to the carrier molecule ex vivo, but they can be joined together at the site of action.

A further embodiment of the present invention thus relates to an adduct or a conjugate or a complex of a carrier molecule and the ligand compound as defined above.

Preferred carrier molecules in the adduct according to the invention are as defined above.

A further embodiment of the present invention relates to a process for preparation of an adduct as defined above, comprising the steps:
(i) Preparation of the ligand compound defined above and
(ii) Bringing the ligand compound into contact with the carrier molecule.

Bringing them into contact preferably comprises the step of oral administration of the ligand compound and/or the step of injection of the ligand compound into an organism, more preferably into the bloodstream. As explained above, this approach makes it possible by the fact that the carrier molecule, for example albumin, does not have to be isolated, and moreover, further material and time savings are achieved, because a synthesis step outside the organism is avoided.

After synthesis of the therapeutically and/or diagnostically active substance, an injectable pharmaceutical preparation containing the therapeutically or diagnostically active substance is prepared in a suitable liquid vehicle. The therapeutically and/or diagnostically active substance generally is present as a solid substance or as a solution, wherein the usual vehicles and/or pharmaceutical excipients can be added such as polysorbates, glucose, lactose, mannose, mannitol, citric acid, trometamol, triethanolamine or aminoacetic acid. The injectable pharmaceutical preparation must be prepared in such a way that the therapeutically or diagnostically active substance is not deactivated, cleaved, or hydrolyzed by dissolving in the injectable liquid vehicle. Furthermore, it must be ensured that the acid-labile bond in the pharmacologically active substance, which for example is an ester, acetal, ketal, imine, hydrazone, carboxylhydrazone, or sulfonylhydrazone bond, is not hydrolyzed. Generally, the pH value is in the range from pH 5.0 to 9.0, preferably from pH 6.0 to pH 8.0.

The liquid vehicles used are approximately isotonic buffers, for example phosphate, acetate, or citrate buffers, such as for example 0.004 M sodium phosphate, 0.15 M NaCl-pH 6.0-7.0 or 0.01 M sodium acetate, 0.15 M NaCl-pH 5.0-6.5. The liquid vehicle used may also be an isotonic sodium chloride solution. The buffers may contain conventional vehicles and/or excipients to ensure that they are isotonic, such as for example polysorbates, glucose, lactose, mannose, mannitol, citric acid, trometamol, triethanolamine or aminoacetic acid.

The solubility of the therapeutically or diagnostically active substance in the injectable liquid vehicle may be improved by means of pharmaceutical solvents such as for example ethanol, isopropanol, 1,2-propylene glycol, glycerol, macrogols, polyethylene glycols or polyethylene oxides or by means of a solubilizer, for example, Tween, Cremophor or polyvinylpyrrolidone. For this purpose, the therapeutically or diagnostically active substance is dissolved in either the pharmaceutical solvent and solubilizer, respectively, and then diluted with saline buffer, or a liquid vehicle, containing the saline buffer and at least one pharmaceutical solvent and solubilizer, respectively, is used to directly dissolve the pharmacologically active substance. The concentration of the pharmaceutical solvent and solubilizer, repectively, in this case does not exceed the quantities specified by the Pharmaceutical-Products Act.

The process of dissolving the therapeutically or diagnostically active substance in the liquid vehicle is generally completed within a few minutes, so that an injectable pharmaceutical preparation can be provided for a patient at the patient's bedside.

In a further embodiment, the process according to the invention comprises the further step of preparation of the carrier molecule, and the ligand compound is brought into contact with the carrier molecule ex vivo. In this way, if necessary, the selectivity of the ligand compound for a carrier molecule, for example a transport protein such as albumin or a transport protein that occurs in small amounts in the blood, such as for example transcortin, can be improved.

A further embodiment of the present invention relates to a pharmaceutical product containing a ligand compound as defined above and/or an adduct as defined above, and optionally at least one pharmaceutically acceptable vehicle and/or excipient and/or diluent. The pharmaceutical product according to the invention can preferably be used to treat cancers, autoimmune disorders, acute or chronic inflammatory diseases that are caused by viruses or microorganisms, such as for example bacteria and/or fungi.

A further embodiment of the present invention relates to a diagnostic kit containing a ligand compound as defined above and/or an adduct as defined above. The diagnostic kit according to the invention can be used preferably to detect the above defined diseases and/or to detect carrier molecules and/or to determine their distribution in the body.

The therapeutic and/or diagnostic ligand systems described above represent formulations of the therapeutic and/or diagnostic agents that, because of their affinity for certain carrier molecules, decisively alter and improve the pharmacokinetic profile of the therapeutic or diagnostic agents. After the ligand compound has been brought into contact with the respective carrier molecule, for example a transport protein such as albumin, within a body fluid or even outside the body, it binds to the carrier molecule due to physical interactions, in order to be present as a transport form so that the therapeutic and/or diagnostic agent contained in the ligand compound is transported to the target site and/or released in a dosed form.

The following examples explain the present invention in more detail.

EXAMPLES

All compounds were characterized by $^1$H and $^{13}$C NMR. silica gel 60, 0.06 mm-0.1 mm was used for column chromatography.
Preparation of Carrier-molecule-Affinitive Ligand Compound According to the Invention BC-DOX1

Bromcresol green sulfonic acid hydrazide was reacted with the cytostatic agent doxorubicin to form the corresponding sulfonic acid hydrazone derivative (abbreviated as BC-DOX1 in the following):

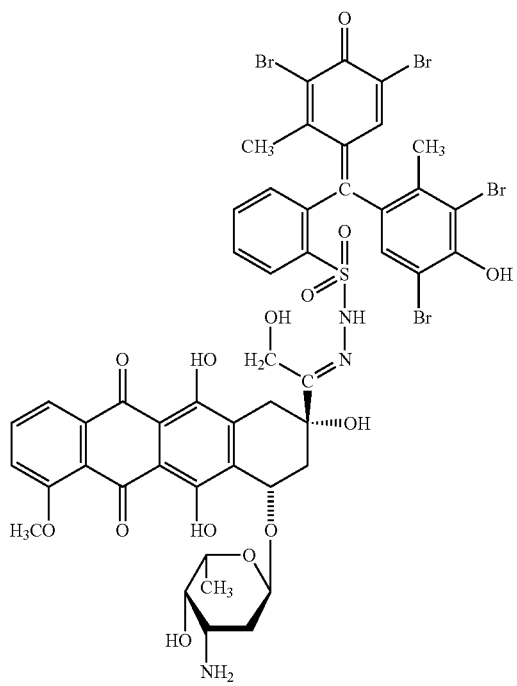

Bromcresol green sulfonic acid hydrazide in this case was prepared in two steps, as explained below.
1. Reaction of bromcresol green sulfonic acid sodium salt with N,N'-dicyclohexylcarbodiimide and a ten-fold excess of tert-butylcarbazate in absolute tetrahydrofuran (THF). The product was isolated on silica gel. THF:hexane=3:2.
2. Cleavage of the BOC protecting group with trifluoroacetic acid and precipitation of the hydrazide with ether.

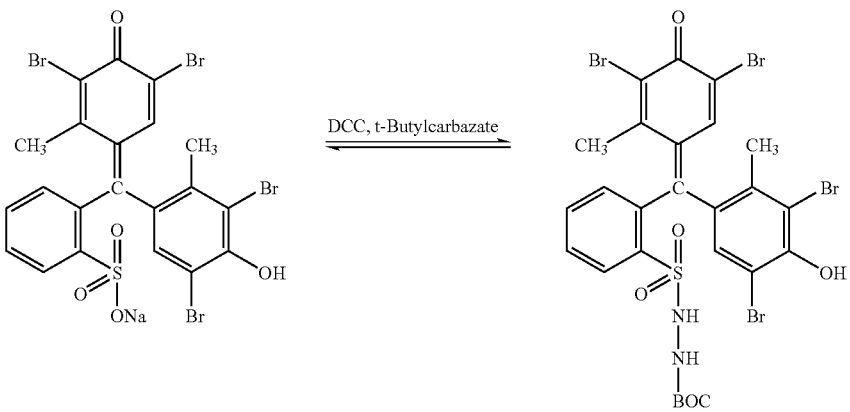

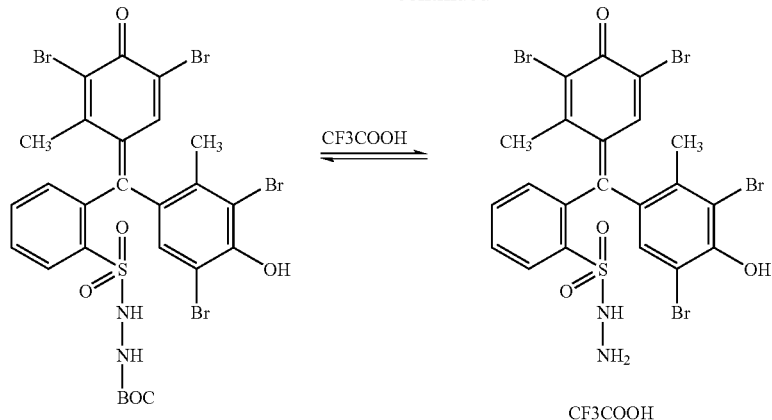

Synthesis of Bromcresol Green Sulfonic Acid Hydrazide:

4.32 g (6 mmol) bromcresol green sulfonic acid sodium salt and 7.93 g (60 mmol) tert-butylcarbazate are dissolved in 50 ml dry tetrahydrofuran and mixed with 1.36 g (6.6 mmol) N,N'-dicyclohexylcarbodiimide (DCC) dissolved in 20 ml dry tetrahydrofuran. The reaction mixture is stirred for 16 h at room temperature, filtered and the solvent is removed under vacuum. The oily residue is purified by column chromatography (silica gel; tetrahydrofuran:hexane=3:2). After drying under high vacuum; 300 mg bromcresol green sulfonic acid tert-butylcarbazate ester is obtained; Rf-value (tetrahydrofuran : hexane=3:2)=0.35.

200 mg bromcresol green sulfonic acid tert-butylcarbazate ester is dissolved in 1.0 ml trifluoroacetic acid and stirred for 1 h at room temperature. The trifluoroacetic acid is removed under vacuum and the preparation is treated with 10 ml dry ether, so that after filtering out the solid and washing with n-hexane, 180 mg bromcresol green sulfonic acid hydrazide trifluoroacetate salt is obtained.

Synthesis of BC-DOX-1:

30 mg (0.05 mmol) doxorubicin and 123 mg (0.15 mmol) bromcresol green sulfonic acid hydrazide trifluoroacetate salt and 10 µl trifluoroacetic acid are dissolved in 10 ml absolute ethanol and stirred for 24 hours in the dark at room temperature. Then, it is concentrated to ~5 ml under vacuum, and the product is brought to cloudiness with 50 ml anhydrous ethyl acetate and then set aside at +5° C. for 16 h. The precipitate is obtained by centrifugation. Then, it is washed twice with 6 ml ethyl acetate and, after drying under high vacuum, 45 mg of product is obtained. Rf=0.16 (reversed phase, 50% $CH_3CN$/50% $K_2HPO_4$ pH 7.0, +2 g/l heptanesulfonic acid)

Binding Behavior with Human Serum Albumin

Bromcresol green or bromcresol green sulfonic acid have binding constants relative to human serum albumin (HSA) of log $K_A \gg 10^7$, and even after incubation times of only a few seconds with HSA (mole ratio 1:1 for physiological concentrations) cannot be isolated by size-exclusion chromatography, for example with Sephadex® G-25, but, in contrast to free doxorubicin, elute together with HSA.

Furthermore, bromcresol green or bromcresol green sulfonic acid do not exhibit high affinity for other plasma proteins. When bromcresol green sulfonic acid is incubated with transferrin, bromcresol green sulfonic acid could be almost completely recovered by size-exclusion chromatography with Sephadex® G-25.

In the incubation experiments described above, the sulfonic acid hydrazone derivative BC-DOX1 exhibits behavior like that of bromcresol green or bromcresol green sulfonic acid.

Thus the carrier-molecule-affinitive ligand compound BC-DOX1 according to the invention displays a very high binding constant relative to the transport protein human serum albumin that surprisingly is several orders of magnitude greater than that of free doxorubicin. Thus BC-DOX1, after being brought into contact with HSA or after injection into the bloodstream, is tightly bound to that blood protein. Since BC-DOX1 in addition has a sulfonylhydrazone bond as an acid-labile bond between the carrier-molecule-affinitive substance and the cytostatic agent, in the acid environment of tumor tissue or in the acid intracellular compartments of the tumor cell, doxorubicin is released as the active substance so it can exert its therapeutic effect there.

Preparation of Doxorubicin Derivatives with Albumin-Binding Ligands (Crocein Orange, Stearic Acid Hydrazide)

Preparation of Doxorubicin Derivative of Crocein Orange Sulfononic Acid Hydrazide (DOXO-CROC)

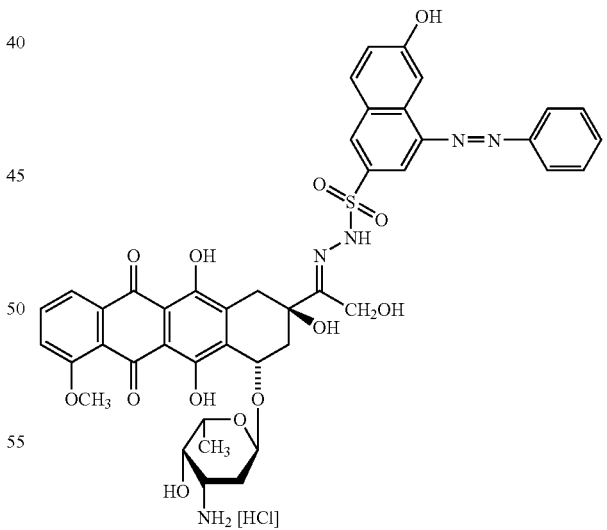

Preparation of Crocein Orange G Acid Chloride 10 g (28.5 mmol) crocein orange G (sodium salt) and 20 g (96.0 mmol) phosphorus pentachloride are heated as the solid powder for 45 min under reflux at 150° C. After cooling, the reaction mixture is taken up in 150 ml dry diethyl ether, filtered and precipitated with 250 ml dry n-hexane. The preparation is stored for 12 h at −20° C. Then, the precipitate is filtered out and washed four times with 60 ml n-hexane each.

After the precipitate is dried under high vacuum, 3.2 g is obtained as an orange powder. Rf=0.48 (tetrahydrofuran)

Preparation of Crocein Orange G Acid Hydrazide 3.65 g (10.5 mmol) crocein orange acid chloride is dissolved in 10 ml dry tetrahydrofuran. 2.09 g (15.8 mmol) tert-butylcarbazate, dissolved in 15 ml dry tetrahydrofuran, is added with stirring. Then, at room temperature 1.46 ml triethylamine, dissolved in 5 ml dry tetrahydrofuran, is added and it is stirred for 16 h. The preparation is filtered and the solvent is drawn off under vacuum. The oily residue is taken up in 50 ml ethyl acetate and extracted once with 100 ml 0.01 N HCl and twice with 75 ml $H_2O$ each. The organic phase is dried over $Na_2SO_4$ and the solvent is drawn off under vacuum. The residue is purified by column chromatography (silica gel; ethyl acetate:n-hexane=1:2). After drying under high vacuum, 2.45 g crocein orange acid tert-butylcarbazate is obtained as a red oil; $R_f$=0.5 (ethyl acetate:n-hexane=1:2).

2.0 g crocein orange acid tert-butylcarbazate is dissolved in 4.0 ml trifluoroacetic acid at room temperature, and the mixture is stirred for 30 min. The trifluoroacetic acid is removed under high vacuum, so that 1.9 g crocein orange acid hydrazide (trifluoracetate salt) is obtained; $R_f$=0.25 (ethyl acetate:n-hexane=1:2).

200 mg (0.35 mmol) doxorubicin, 790 mg (1.73 mmol) crocein orange acid hydrazide (trifluoracetate salt) and 60 μl trifluoroacetic acid are dissolved in 40 ml absolute methanol and stirred overnight in the dark at room temperature. Then, the mixture is filtered, the solvent is removed under vacuum down to a volume of about 30 ml, and the product is precipitated with 80 ml acetonitrile (HPLC grade). The mixture is stored for 12 h at −20° C. Then, the precipitate is centrifuged off and washed with acetonitrile until the supernatant is colorless. Finally, it is washed once with 10 ml diethyl ether and, after drying under high vacuum, 250 mg of product is obtained. Rf=0.14 (reversed phase, 50% $CH_3CN$/50% $K_2HPO_4$, pH 7.0+2 g/l heptanesulfonic acid)

Preparation of Doxorubicin Hydrazone Derivative of Crocein Orange and Hexaethylene Glycol as Spacer (DOXO-CROC-HEXA)

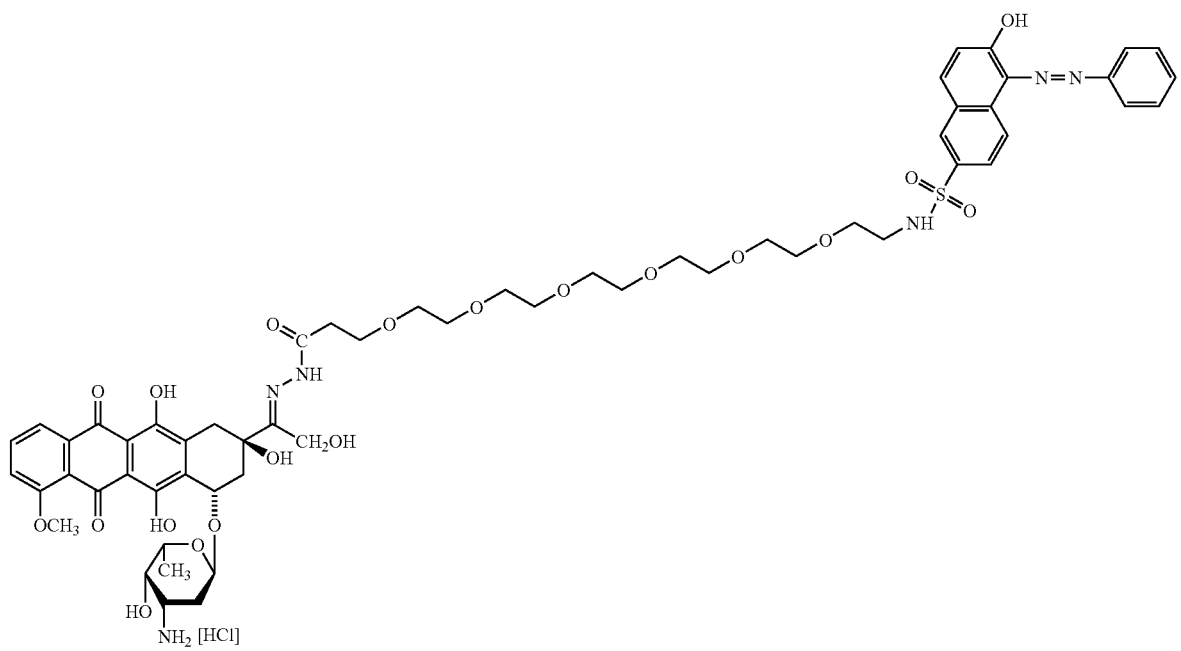

Synthesis of Aminohexaethylene Glycol t-butylcarbazate Spacer (4)
Synthesis Route:

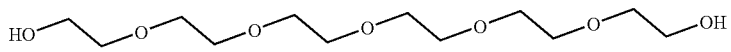

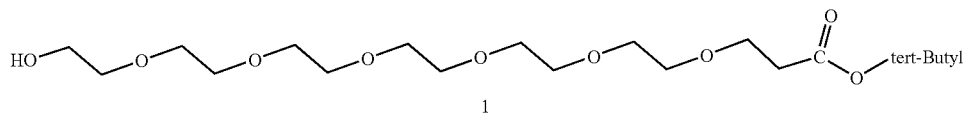

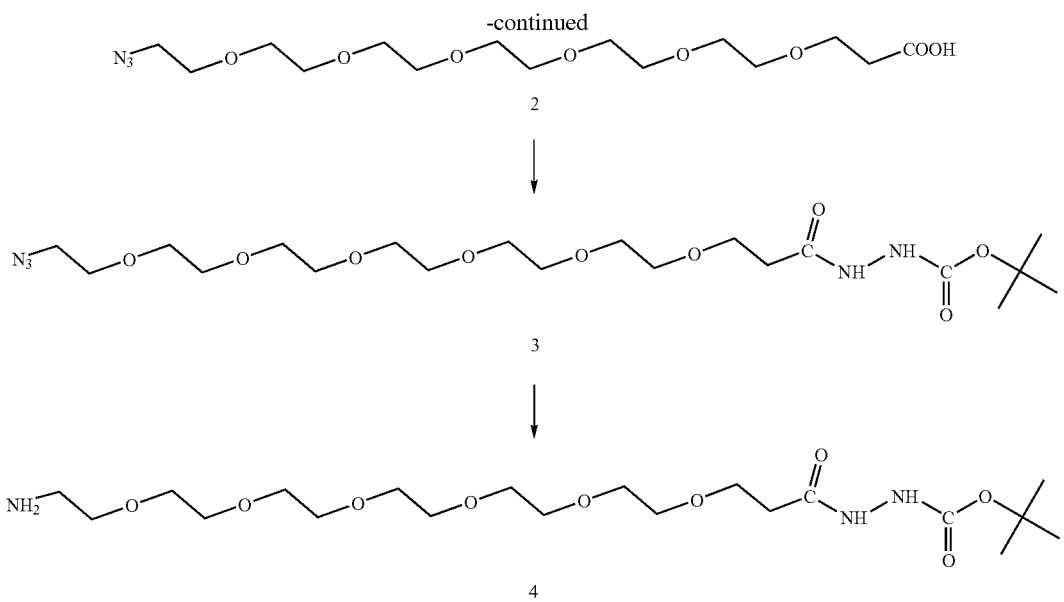

Synthesis for Step 1 (1)

51.05 g (175.4 mmol) hexaethylene glycol is dissolved in 90 ml absolute THF and mixed with 211 mg (1.8 mmol) potassium tert-butylate. 9.2 ml acrylic acid tert.-butyl ester, dissolved in 15 ml dry THF, is added dropwise with stirring at room temperature over a period of 30 min. The preparation is stirred for 16 h at room temperature. The reaction mixture is neutralized, with stirring, with 2 ml of 1 N HCl. The solvent is removed under vacuum, and the oily residue is taken up in 50 ml of saturated NaCl solution and extracted three times with 50 ml dichloromethane. The organic phases are combined, dried over $Na_2SO_4$, filtered and the solvent is removed under vacuum. The oily residue is purified by column chromatography (silica gel; ethyl acetate:methanol=4:1). After drying under high vacuum, 20.25 g is obtained as a light yellowish oil. Rf=0.63 (ethyl acetate: methanol=4:1)

Synthesis for Step 2 (2)

20.25 g (49.4 mmol) of 1 is dissolved in 60 ml of absolute THF. 5.73 ml (74.1 mmol) methanesulfonyl chloride followed by 10.3 ml triethylamine (74.1 mmol) are added to this solution with stirring at room temperature. The mixture is stirred for 16 h at room temperature. The reaction mixture is filtered and the solvent is removed under vacuum. After drying under high vacuum, 26.98 g is obtained as a light brownish oil, which is dissolved in 90 ml of dry acetonitrile and mixed with 7.19 g (110.6 mmol) sodium azide. The reaction mixture is stirred for 36 h under reflux. The reaction mixture is filtered and the solvent is removed under vacuum. After drying under high vacuum, 23.06 g is obtained as a light brownish oil, which is dissolved in 30 ml dichloromethane. 32.5 ml trifluoroacetic acid is added dropwise with stirring at room temperature over a period of 10 min. The mixture is stirred for 2 h. The solvent and the trifluoroacetic acid are evaporated under high vacuum. The oily residue is purified by column chromatography (silica gel; ethyl acetate:methanol=6:1+0.5% acetic acid). After drying under high vacuum, 16.1 g is obtained as an oil.

Rf=0.2 (ethyl acetate:methanol=6:1+0.5% acetic acid)

Synthesis for Step 3 (3)

14.03 g (37.21 mmol) 2 and 5.41 g tert-butylcarbazate are dissolved in 420 ml apure dichloromethane and then 6.34 ml diisopropylcarbodiimide is added dropwise over a 2 min period. The mixture is stirred for 4 h. The reaction mixture is filtered and the solvent is evaporated under vacuum. The oily residue is purified by column chromatography (silica gel; ethyl acetate:methanol=12:1). After drying under high vacuum, 10.2 g is obtained as an oil. Rf=0.23 (ethyl acetate:methanol=8:1)

Synthesis for Step 4 (4)

10.2 g (20.7 mmol) 3 is dissolved in 100 ml absolute methanol and 1.4 g 10% palladium on activated charcoal is added in portions under nitrogen. Then 5.4 g (82.9 mmol) ammonium formate, dissolved in 60 ml absolute methanol, is added and is stirred for 12 h at 50° C. The reaction mixture is filtered through Cellite and the solvent is removed under vacuum. The oily residue is purified by column chromatography (silica gel; methanol+1% triethylamine).

After drying under high vacuum, 8.53 g is obtained as an oil.

Rf=0.22 (methanol+1% triethylamine)

Synthesis of Hexaethylene Glycol Hydrazide Derivative of Crocein Orange (5):

120 mg (0.24 mmol) 4 and 84 mg (0.24 mmol) crocein orange acid chloride are dissolved in 2 ml dry tetrahydrofuran and then mixed with 68 pi triethylamine. The mixture is stirred for another 2.5 h. The solvent is removed under vacuum. After drying under vacuum, 200 mg is obtained as a light yellowish oil, which is mixed with 400 µl trifluoroacetic acid and stirred for 10 min. The trifluoroacetic acid is removed under vacuum and the oily residue is purified by column chromatography (silica gel; ethyl acetate:methanol=2:1). After drying under high vacuum, 137 mg of product (trifluoroacetate salt) is obtained as a light yellowish oil; Rf=0.3 (ethyl acetate/methanol=2:1).

Synthesis of DOXO-CROC-HEXA:

25 mg (0.04 mmol) doxorubicin and 104.5 mg (0.15 mmol) crocein orange hexaethylene glycol hydrazide (trifluoroacetate salt) (5) are dissolved in 5 ml absolute methanol and stirred for 24 hours in the dark at room temperature. Then, the product is precipitated with 75 ml ethyl acetate (HPLC grade) and centrifuged for 10 minutes at +4° C. Then, it is washed twice with 10 ml ethyl acetate. After drying under high vacuum, 35 mg of product is obtained. Rf=0.11 (reversed phase, 50% $CH_3CN$/50% $K_2HPO_4$, pH 7.0, +2 g/l heptanesulfonic acid)

Preparation of Doxorubicin Hydrazone Derivative of 2,3,5-triiodobenzoic Acid and Hexaethylene Glycol as Spacer (DOXO-TIB-HEXA)

Synthesis of DOXO-TIB-HEXA:

30 mg (0.06 mmol) doxorubicin and 150 mg (0.15 mmol) triiodobenzoic acid hexaethylene glycol hydrazide (trifluoro-

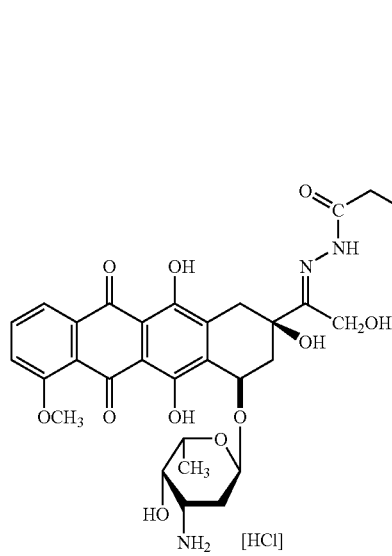

Synthesis of the Hexaethylene Glycol Hydrazide Derivative of 2,3,5-triiodobenzoic Acid (6):

124 mg (0.26 mmol) 4, 132.8 mg (0.26 mmol) 2,3,5-triiodobenzoic acid and a spatula-tipful of dimethylaminopyridine are dissolved in 3.0 ml dry tetrahydrofuran. The mixture is cooled down to 0° C. and mixed with 40 µl diisopropylcarbodiimide. The reaction mixture is stirred for another 12 h, protected from light. The solvent is removed under vacuum. The oily residue is purified by column chromatography (silica gel; tetrahydrofuran:hexane=8:1). After drying under high vacuum, 195 mg of product (hexaethylene glycol tert-butylcarbazate derivative of 2,3,5-triiodobenzoic acid) is obtained as a light yellowish oil; Rf=0.46 (tetrahydrofuran:hexane=8:1). 160 mg of the hexaethylene glycol tert-butylcarbazate derivative of 2,3,5-triiodobenzoic acid is dissolved in 500 µl trifluoroacetic acid and stirred for 30 min at room temperature. The trifluoroacetic acid is removed under vacuum, so that 150 mg of the hexaethylene glycol hydrazide derivative of 2,3,5-triiodobenzoic acid is obtained as an oil, which is directly used in the following.

acetate salt) are dissolved in 6 ml absolute methanol and stirred for 24 hours in the dark at room temperature. Then the product is precipitated with 60 ml ethyl acetate (HPLC grade) and centrifuged for 10 minutes at +4° C. Then, it is washed twice with 6 ml ethyl acetate, and after drying under high vacuum, 42 mg of product is obtained. Rf=0.06 (reversed phase, 50% $CH_3CN$/50% $K_2HPO_4$ pH 7.0, +2 g/l heptanesulfonic acid).

Preparation of Doxorubicin Hydrazone Derivative of Stearic Acid Hydrazide (DOXO-SAH)

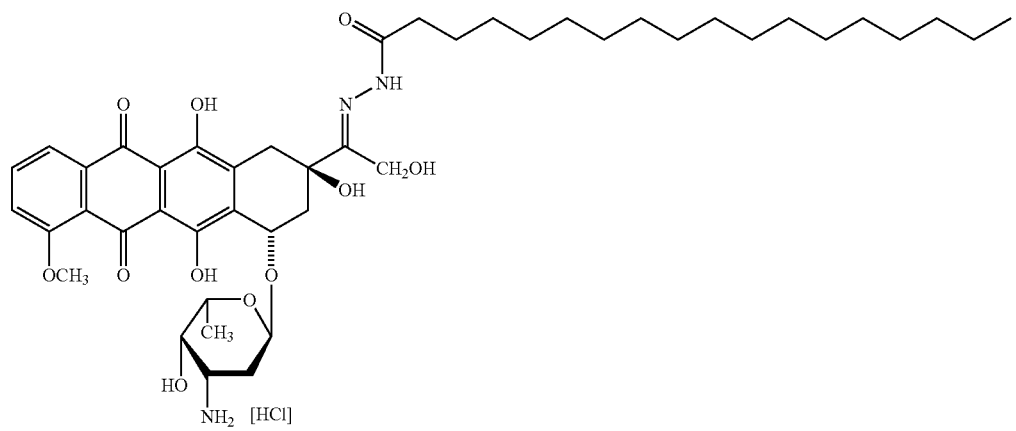

Preparation of Stearic Acid Hydrazide

Stearic acid tert-butylcarbazate: 6.06 g (20 mmol) stearic acid chloride is dissolved in 10 ml dry THF. 2.77 ml (20 mmol) triethylamine and 2.91 g (22 mmol) tert-butylcarbazate, dissolved in 10 ml THF, are added dropwise with stirring at room temperature over a 10 min period, and the mixture is stirred for 30 min. The reaction mixture is filtered and the solvent is removed under vacuum. The oily residue is taken up in 50 ml ethyl acetate and extracted twice with 70 ml $H_2O$.

The organic phase is dried over $Na_2SO_4$ and filtered, and the solvent is evaporated under vacuum. The oily residue is dissolved in 50 ml warm ethanol and stored for 12 h at +4° C. The white precipitate is filtered and washed twice with 30 ml ethanol each. After drying under high vacuum, 3.6 g stearic acid tert-butylcarbazate is obtained; Rf=0.9 (ethyl acetate/n-hexane 2/1).

Stearic acid hydrazide: 1.8 g (4.52 mmol) stearic acid tert-butylcarbazate is dissolved in 3 ml trifluoroacetic acid, stirred for 15 min and the solvent is removed under vacuum. The mixture is treated with 30 ml dry ether and the precipitate formed is filtered out and washed twice with 50 ml dry diethyl ether. After drying under high vacuum, 1.03 g stearic acid hydrazide is obtained; Rf=0.66 (ethyl acetate/methanol 1/1)

Synthesis of DOXO-SAH:

50 mg (0.09 mmol) doxorubicin hydrochloride and 42 mg (0.1 mmol) stearic acid hydrazide trifluoroacetate are dissolved in 30 ml methanol (HPLC grade) and stirred for 18 hours in the dark at room temperature. Then, the product is precipitated with 40 ml acetonitrile (HPLC grade). The precipitate is centrifuged for 10 minutes at room temperature, then washed twice with 30 ml acetonitrile and once with 10 ml diethyl ether, and after drying under high vacuum, 60 mg of product is obtained; Rf=0.15 (reversed phase, 50% $CH_3CN$/50% 20 mM $K_2HPO_4$ pH 7.0, +2 g/l heptanesulfonic acid).

Binding Behavior with Human Serum Albumin

A Scatchard plot is used to determine the binding constants relative to human serum albumin (HSA from the Dessau company, Germany) at pH 7.4 by means of equilibrium dialysis (equilibrium dialyzer from Spectrum, Inc., USA; dialysis membrane: cut-off MW 10000) for the prepared doxorubicin derivatives, all including an acid-labile hydrazone bond as the predetermined breaking point, and for doxorubicin. The results are summarized in Table 2 below.

TABLE 2

| Substance | $K_A$ relative to HSA |
|---|---|
| Doxorubicin | $2.9 \times 10^3$ $2.7 \times 10^{3}$* |
| DOXO-CROC | $6.4 \times 10^6$ |
| DOXO-CROC-HEXA | $7.2 \times 10^7$ |
| DOXO-TIB-HEXA | $5.5 \times 10^5$ |
| DOXO-SAH | $6.1 \times 10^6$ |

*Literature value (Demant et al., Biochemical Pharmacology 55, 27-32, 1998)

The albumin-binding ligand compounds of doxorubicin have HSA binding constants that are 2-3 orders of magnitude higher than the binding constants for doxorubicin.

Furthermore, the albumin-binding ligand compounds of doxorubicin, after incubation times of only a few seconds with HSA or blood plasma (molar ratio 1:1, pH 7.0-7.5), cannot be isolated by size-exclusion chromatography, for example with Sephadex® G-25, but, in contrast to free doxorubicin, elute together with HSA.

Furthermore, the albumin-binding ligand compounds of doxorubicin do not exhibit high affinity for other plasma proteins: If they are incubated with transferrin, the albumin-binding ligand compounds of doxorubicin are almost completely recovered by size-exclusion chromatography with Sephadex® G-25.

Thus, the carrier-molecule-affinitive ligand compounds of doxorubicin according to the invention display a very high binding constant relative to the transport protein human serum albumin, which surprisingly is several orders of magnitude greater than that of free doxorubicin. Thus, the albumin-binding ligand compounds of doxorubicin, after being brought into contact with HSA or after injection into the bloodstream, have a strong interaction with this blood protein. Since the albumin-binding ligand compounds of doxorubicin have a hydrazone bond as an acid-labile bond between the carrier-molecule-affinitive substance and the cytostatic agent, in the acid environment of tumor tissue or in the acid intracellular compartments of the tumor cell, doxorubicin can be released as the active substance so it can exert its therapeutic effect there.

The antitumor effect of DOXO-CROC was studied in a melanoma xenograft model (MV-3). The data are summarized in Table 3 below:

TABLE 3

| Substance | Number of nude mice | Treatment scheme | Mortality | Optimum T/C-value (%)* |
|---|---|---|---|---|
| NaCl | 8 | 3× (Day 10, 17, 24) | — | |
| DOXO-CROC | 8 | 3 × 16 mg/kg -i.p. Tween (Day 10, 17, 24) | — | 37 |

*Ratio of tumor sizes in treated group compared to control group

Treatment with DOXO-CROC was tolerated very well: The decrease in body weight during treatment with DOXO-CROC was only −3%; growth of the subcutaneously growing tumors was able to be inhibited by approximately more than 60% compared with the control.

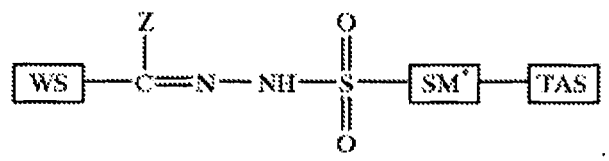

The invention claimed is:

1. A carrier molecule comprising:
   (a) at least one anthracycline, and
   (b) at least one albumin-affinitive substance selected from phthalocyanines, coumarins, flavonoids, tetracyclines, naphthalenes, aryl- and heteroarylcarboxylic acids, long-chain fatty acids, pyrroles, aromatic acids substituted with 2-5 chlorine atoms, aromatic acids substituted with 2-5 bromine atoms, aromatic acids substituted with 2-5 iodine atoms, organic dyes, benzophenones, phthalimides and isophthalimides, phthalic acids and isophthalic acids, quinolines and isoquinolines, anthraquinones, anthracenes, phenanthrenes, phenanthrolines, benzylidenes, diphenyls and biphenyls, indoles, indanes, hippuric acids, imidazoles and benzimidazoles, quinoxalines, pyridines, pyrimidines, piperidines, sarcosines, oxazoles, oxadiazoles, isoxazoles, pyrazoles, triazoles and tetrazoles, benzothiazoles, triazines, morpholines, chromenes, trisubstituted ethanoic and propanoic acids, tetrasubstituted ethanoic and propanoic acids, and pentasubstituted ethanoic and propanoic acids, stilbenes, tryptophan analog compounds, iodophenoxic acid, and 2,3,5-triiodobenzoic acid;
   wherein said albumin-affinitive substance binds non-covalently to albumin with an association constant $K_A$ relative to albumin greater than $10^3$ $M^{-1}$ via a non-covalent bond; and wherein said (a) anthracycline is linked to said (b) albumin-affinitive substance through an acid labile linkage selected from ester, acetal, ketal, imine, hydrazone, carboxylhydrazone, and sulfonylhydrazone linkages or through a linkage which is enzymatically cleavable within the body and which is not a peptide bond.

2. The carrier molecule according to claim 1, further comprising:
   (c) a spacer molecule inserted between said acid labile or enzymatically cleavable linkage and said (b) albumin-affinitive substance.

3. The carrier molecule according to claim 2, wherein said spacer molecule comprises a peptide sequence that contains at least one protease cleavage sequence.

4. The carrier molecule according to claim 2, wherein said spacer molecule contains at least one acid-labile bond selected from ester, acetal, ketal, imine, hydrazone, carboxylhydrazone, and sulfonylhydrazone linkages.

5. The carrier molecule according to claim 2, wherein said spacer molecule comprises at least one substituted or unsubstituted aryl residue or a substituted or unsubstituted, branched-chain or unbranched-chain aliphatic alkyl residue wherein said aliphatic alkyl residue comprises 1 to 20 carbon atoms, which can be partially replaced by oxygen or nitrogen atoms.

6. Adduct of the carrier molecule according to claim 1 and albumin, wherein binding between said carrier molecule and albumin is non-covalent.

7. The carrier molecule according to claim 2, wherein said spacer molecule contains at least one protease-sensitive peptide bond; and at least one acid-labile bond selected from ester, acetal, ketal, imine, hydrazone, carboxylhydrazone, and sulfonylhydrazone linkages.

8. The carrier molecule according to claim 1, wherein the albumin-affinitive substance is selected from pyrroles in the form of dipyrroles and tripyrroles, cyclic and linear tetrapyrroles, and organometallic compounds thereof.

9. A carrier molecule comprising:
   (a) at least one therapeutically and/or diagnostically active substance and
   (b) at least one albumin-affinitive substance selected from dyes from the class of phthaleins and sulfophthaleins, azo dyes, aromatic compounds substituted with 2-5 halogens, and long chain fatty acids;
   wherein said albumin-affinitive substance binds non-covalently to albumin with an association constant $K_A$ relative to albumin greater than $10^3$ $M^{-1}$ via a non-covalent bond;
   wherein said (a) therapeutically and/or diagnostically active substance is linked to said (b) albumin-affinitive substance through an acid labile linkage selected from ester, acetal, ketal, imine, hydrazone, carboxylhydrazone, and sulfonylhydrazone linkages or through a linkage which is enzymatically cleavable within the body and which is not a peptide bond.

10. The carrier molecule according to claim 9, further comprising:
    (c) a spacer molecule inserted between said acid labile or enzymatically cleavable linkage and said (b) albumin-affinitive substance.

11. The carrier molecule according to claim 10, wherein said spacer molecule comprises a peptide sequence that contains at least one protease cleavage sequence.

12. The carrier molecule according to claim 10, wherein said spacer molecule contains at least one acid labile bond selected from ester, acetal, ketal, imine, hydrazone, carboxylhydrazone, and sulfonylhydrazone linkages.

13. The carrier molecule according to claim 9, wherein said therapeutically active substance is selected from a cytostatic agent, a cytokine, an immunosuppressant, an antirheumatic agent, an antiinflammatory agent, an antibiotic, an analgesic, a virostatic agent, and an antimycotic agent.

14. The carrier molecule according to claim 13, wherein said cytostatic agent is selected from anthracyclines, N-nitrosoureas, alkylating agents, purine antagonists, pyrimidine antagonists, folic acid antagonists, taxanes, camptothecines, podophyllotoxins, vinca alkaloids, calicheamicins, maytansinoids, epithilones, and platinum (II) complexes in the cis configuration.

15. The carrier molecule according to claim 9, wherein said diagnostically active substance contains one or more substances selected from radionuclides, ligands comprising radionuclides, positron emitters, NMR contrast media, fluorescent compound(s), and contrast media in the near IR region.

16. The carrier molecule according to claim 10, wherein said spacer molecule comprises at least one substituted or unsubstituted aryl residue or a substituted or unsubstituted, branched-chain or unbranched-chain aliphatic alkyl residue wherein said aliphatic alkyl residue comprises 1 to 20 carbon atoms, which can be partially replaced by oxygen or nitrogen atoms.

17. An adduct of the carrier molecule according to claim 9 and albumin, wherein binding between said carrier molecule and albumin is non-covalent.

18. The carrier molecule according to claim 1, wherein the carrier molecule is selected from
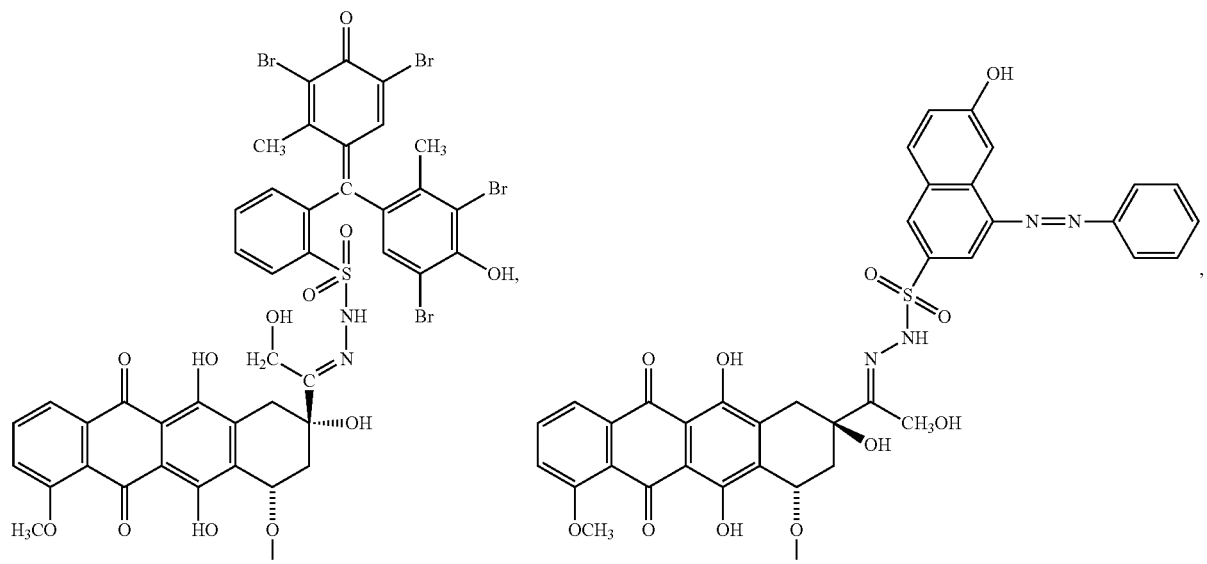
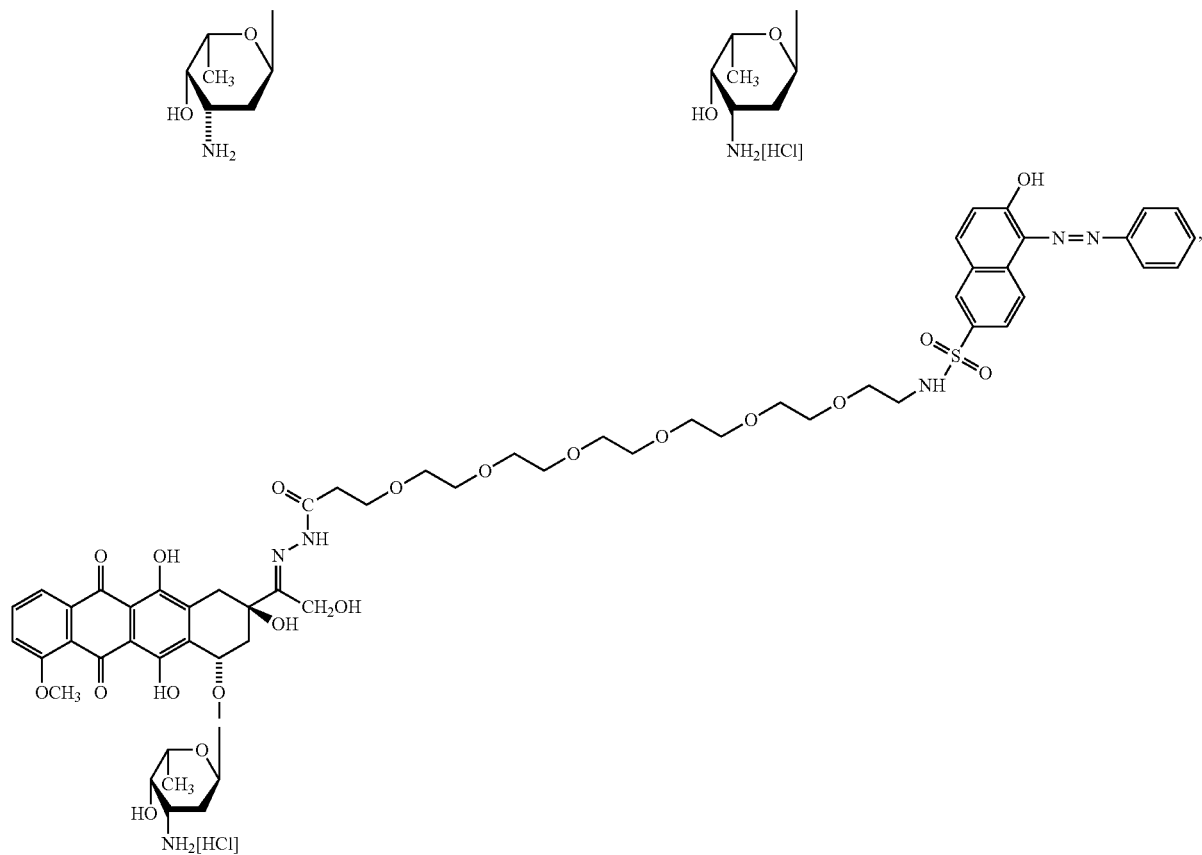

-continued

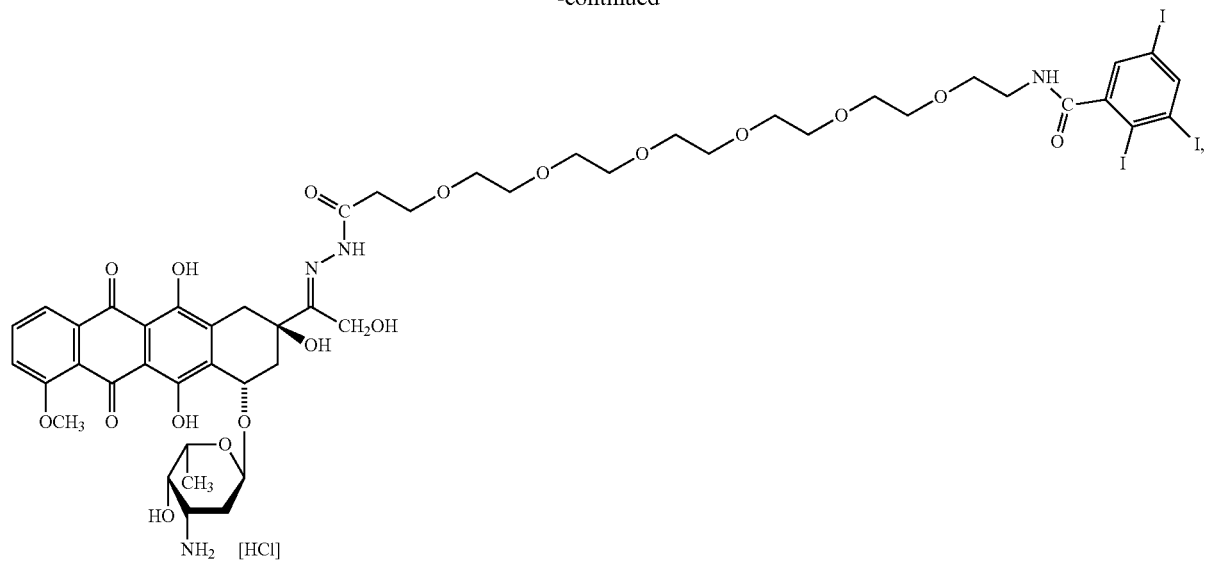

and

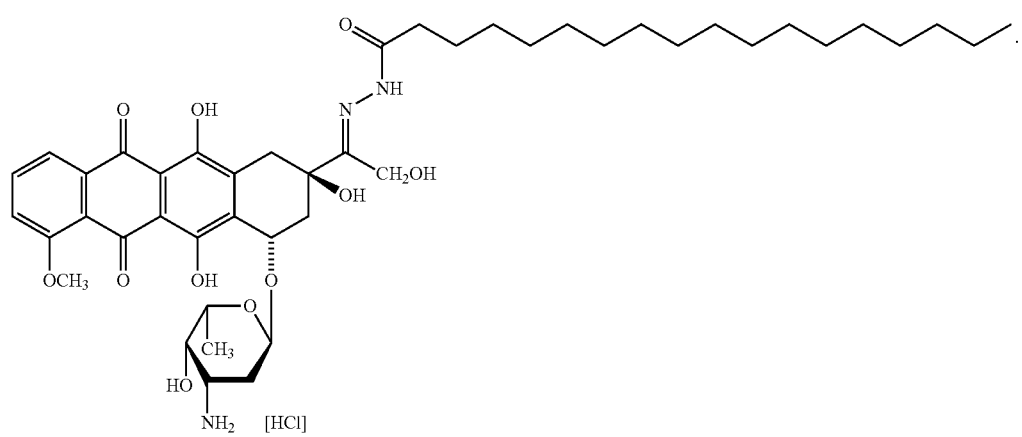

19. The carrier molecule according to claim 1, wherein the albumin-affinitive substance is selected from dyes from the class of phthaleins and sulfophthaleins, azo dyes, aromatic compounds substituted with 2-5 halogens, and long chain fatty acids.

20. The carrier molecule according to claim 1, wherein the anthracycline is selected from doxorubicin, daunorubicin, epirubicin, idarubicin, mitoxantrone, ametantrone, and derivatives thereof.

21. The carrier molecule according to claim 20, wherein the anthracycline is doxorubicin.

22. The carrier molecule according to claim 1, wherein the carrier molecule has a structure selected from

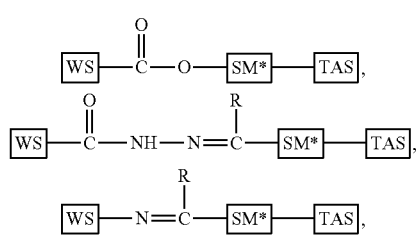

-continued

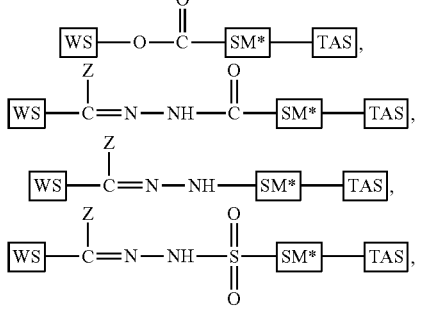

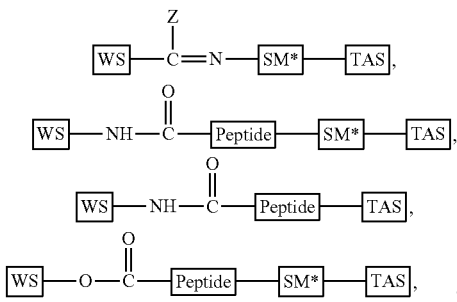

and

-continued

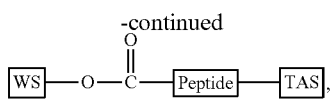

wherein
WS is the anthracycline;
TAS is the albumin-affinitive substance;
SM* is an optional spacer molecule;
R is selected from H, alkyl, phenyl, and substituted phenyl;
Z is a chemical group of the anthracycline;
and Peptide is a peptide chain.

23. The carrier molecule according to claim 22, wherein the carrier molecule has a structure selected from

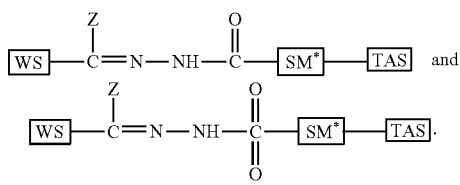

24. A pharmaceutical composition comprising a carrier molecule according to claim 1 and a pharmaceutically acceptable vehicle or excipient.

25. A method of treating cancer comprising administering a carrier molecule according to claim 1 to a patient in need thereof.

26. The method according to claim 25, wherein the anthracycline is selected from doxorubicin, daunorubicin, epirubicin, idarubicin, mitoxantrone, ametantrone, and derivatives thereof.

27. The method according to claim 26, wherein the anthracycline is doxorubicin.

28. A pharmaceutical composition comprising an adduct according to claim 6 and a pharmaceutically acceptable vehicle or excipient.

29. A method of treating cancer comprising administering an adduct according to claim 6 to a patient in need thereof.

30. The carrier molecule according to claim 13, wherein said therapeutically active substance is a cytostatic agent.

* * * * *

UNITED STATES PATENT AND TRADEMARK OFFICE
CERTIFICATE OF CORRECTION

PATENT NO. : 7,902,144 B2  Page 1 of 2
APPLICATION NO. : 10/221544
DATED : March 8, 2011
INVENTOR(S) : Felix Kratz It is certified that error appears in the above-identified patent and that said Letters Patent is hereby corrected as shown below:

In Claim 18, columns 75-76, lines 3-65, please delete the chemical structures on this page and replace with the following:

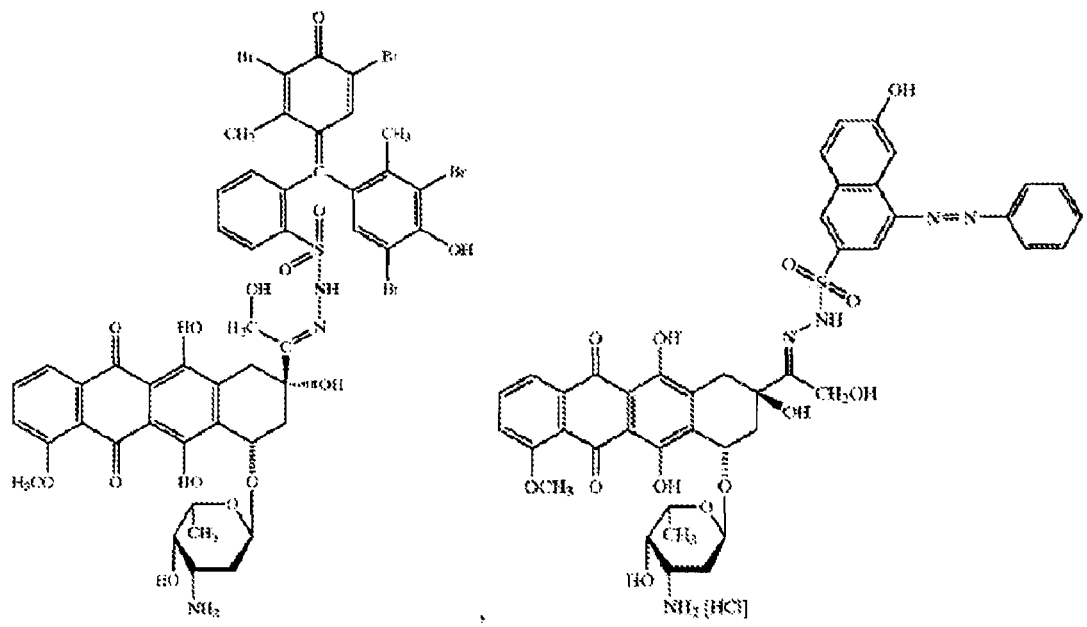

Signed and Sealed this
Twenty-sixth Day of April, 2011

David J. Kappos
*Director of the United States Patent and Trademark Office*

CERTIFICATE OF CORRECTION (continued)
U.S. Pat. No. 7,902,144 B2

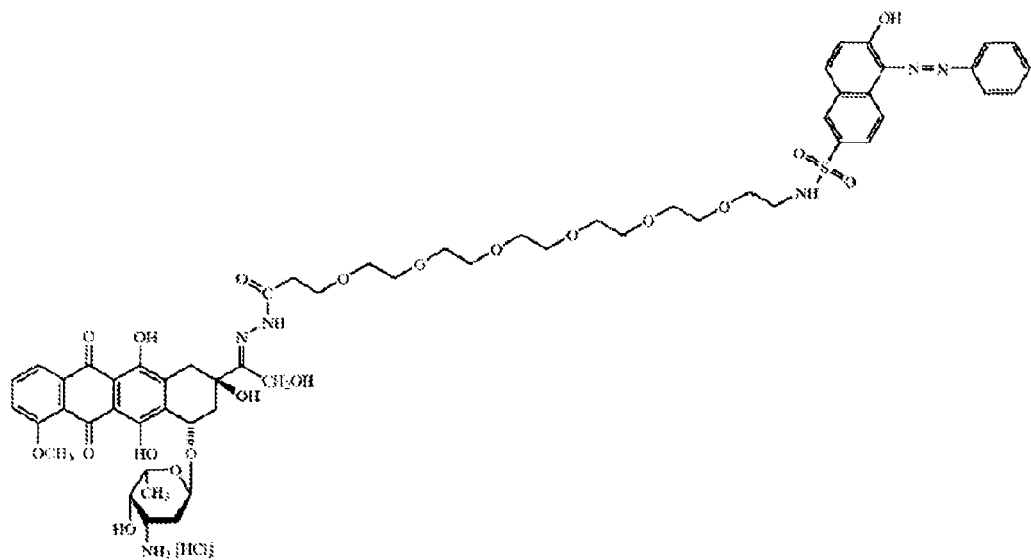

,

In Claim 18, columns 77-78, lines 1-25, please delete the first chemical structure on this page and replace with the following:

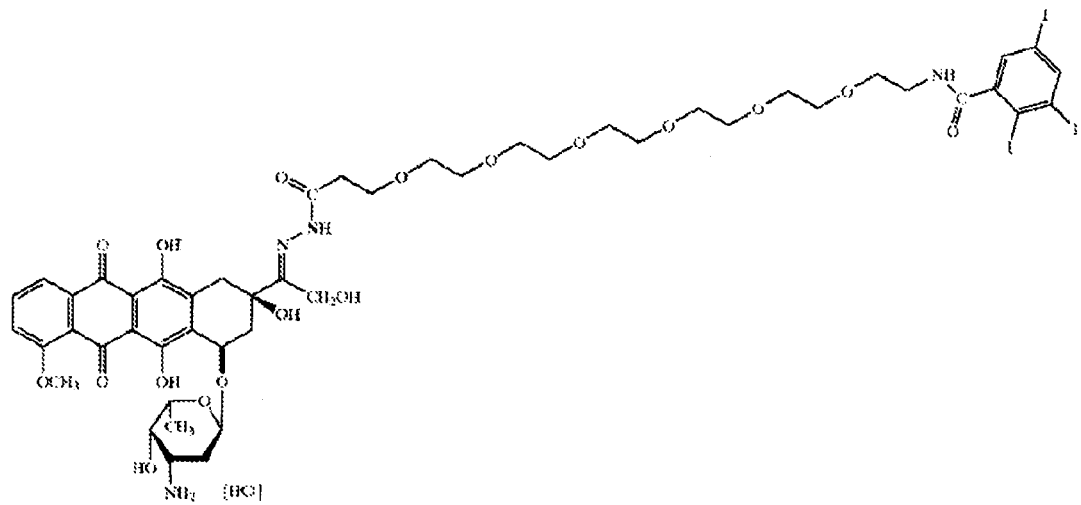

,

In claim 23, column 79, lines 20-24, please replace the second chemical structure with the following: